US011047867B2

(12) United States Patent
Frade López et al.

(10) Patent No.: US 11,047,867 B2
(45) Date of Patent: Jun. 29, 2021

(54) METHOD FOR DETERMINING THE RISK OF DEVELOPING ALZHEIMER'S DISEASE

(71) Applicants: CONSEJO SUPERIOR DE INVESTIGACIONES CIENTÍFICAS, Madrid (ES); TETRANEURON S.L., Madrid (ES)

(72) Inventors: José María Frade López, Madrid (ES); Noelia López Sánchez, Madrid (ES)

(73) Assignees: Consejo Superior de Investigaciones Cientificas, Madrid (ES); TETRANEURON S.L., Madrid (ES)

( * ) Notice: Subject to any disclaimer, the term of this patent is extended or adjusted under 35 U.S.C. 154(b) by 0 days.

(21) Appl. No.: 15/740,888

(22) PCT Filed: Jun. 29, 2016

(86) PCT No.: PCT/ES2016/070485
§ 371 (c)(1),
(2) Date: Dec. 29, 2017

(87) PCT Pub. No.: WO2017/001716
PCT Pub. Date: Jan. 5, 2017

(65) Prior Publication Data
US 2018/0136235 A1 May 17, 2018

(30) Foreign Application Priority Data

Jun. 30, 2015 (ES) .............. ESP201530938

(51) Int. Cl.
*G01N 33/68* (2006.01)
*G01N 33/573* (2006.01)

(52) U.S. Cl.
CPC ....... *G01N 33/6896* (2013.01); *G01N 33/573* (2013.01); *G01N 2333/4703* (2013.01); *G01N 2800/2821* (2013.01); *G01N 2800/50* (2013.01); *G01N 2800/52* (2013.01)

(58) Field of Classification Search
CPC ....... G01N 33/6896; G01N 2333/4703; G01N 2800/2821; G01N 2800/50; G01N 2800/52
See application file for complete search history.

(56) References Cited

U.S. PATENT DOCUMENTS

| 7,682,807 | B2 | 3/2010 | Zhao et al. |
| 9,188,595 | B2 | 11/2015 | Zhao et al. |
| 2005/0059092 | A1 | 3/2005 | Zhao et al. |
| 2010/0278803 | A1 | 11/2010 | Zhao et al. |
| 2015/0018278 | A1 | 1/2015 | Frade Lopez |

FOREIGN PATENT DOCUMENTS

| ES | 2325350 T1 | 9/2009 |
| WO | 2013076331 A1 | 5/2013 |

OTHER PUBLICATIONS

International Search Report and Written Opinion for PCT/ES2016/070485, dated Sep. 1, 2016.
Kohnken R et al. Neuroscience Letters. 2000. vol. 287, pp. 187-190.
Lu KP et al. Trends in Cell Biology. 2002. vol. 12(4), pp. 164-172.
Kang et al., 2014 Korean J Physiol Pharmacol. 18: pp. 447-456.
Zhang et al., 2012 Neurobiol. Aging 33, pp. 2661-2677.
Blast Manual, Altschul, S., et. al., NCBI NLM NIH Bethesda, MD. 20894, Altschul, S., et. al., J. Mol. Biol. 215: pp. 403-410, 1990.
Fernandez et al., 2012 Mol. Psychiatry 17, pp. 705-718.
López-Sänchez and Frade J. Neurosci. 33: pp. 7488-7500, 2013.
Anne M Fagan et al., "Cerebrospinal fluid biomarkers of Alzheimer's disease," Biomark Med., Feb. 1, 2010, pp. 51-63, vol. 4, No. 1.
Noelia Lopez-Sanchez et al., "A Mutant Form of E2F4 Prevents Neuronal Tetraploidization and Cognitive Deficits in 5XFAD Mice Without Affecting Aβ Deposition," Alzheimer's & Dementia: The Journal of the Alzheimer's Association, Jul. 17, 2017, vol. 13, No. 7.
Partial Supplementary European Search Report in EP Application No. 16817300.3, dated Jan. 15, 2019.
Marilyn S. Albert et al., "The diagnosis of mild cognitive impairment due to Alzheimer's disease: Recommendations from the National Institute on Aging-Alzheimer's Association workgroups on diagnostic guidelines or Alzheimer's disease," Alzheimer's & Dementia, Apr. 2011, pp. 270-279, vol. 7.
Anne M Fagan et al., "Cerebrospinal fluid biomarkers of Alzheimer's disease," Biomark Med., Feb. 2010, pp. 51-63, vol. 4, No. 1.
Anthony Brureau et al., "NF-L in cerebrospinal fluid and serum is a biomarker of neuronal damage in an inducible mouse model of neurodegeneration," Neurobiology of Disease, Aug. 2017, pp. 73-84, vol. 104.
Clifford R. Jack Jr. et al., "Introduction to the recommendations from the National Institute on Aging-Alzheimer's Association workgroups on diagnostic guidelines for Alzheimer's disease," Alzheimer's & Dementia, May 2011, pp. 257-262, vol. 7.

(Continued)

*Primary Examiner* — Olga N Chernyshev
(74) *Attorney, Agent, or Firm* — Pilloff Passino & Cosenza LLP; Sean A. Passino; Rachel K. Pilloff

(57) ABSTRACT

The present invention relates to an in vitro method for determining the risk of developing Alzheimer's disease or a cognitive disorder similar to said disease, an in vitro method for designing a personalized therapy in a subject suffering from mild cognitive impairment and an in vitro method for selecting a patient susceptible to be treated with a therapy for the prevention and/or treatment of Alzheimer's or a cognitive disorder similar to said disease based on determining, in a sample from the subject, the level of phosphorylation in threonine residues in E2F4 protein or in a functionally equivalent variant. The invention also relates to the use of E2F4 or a functionally equivalent variant thereof, wherein the E2F4 or variant is phosphorylated in threonine as a marker of the risk of developing Alzheimer's disease or a cognitive disorder similar to Alzheimer's disease. Finally, the invention relates to a kit comprising a reagent capable of determining the level of phosphorylation in threonine residues of E2F4 protein and the use of said kit.

9 Claims, 4 Drawing Sheets

(56) References Cited

OTHER PUBLICATIONS

Beth Adams et al., "Use of a delayed non-matching to position task to model age-dependent cognitive decline in the dog," Behavioural Brain Research, Feb. 2000, pp. 47-56, vol. 108.
Joseph A. Araujo et al., "Further evidence for the cholinergic hypothesis of aging and dementia from the canine model of aging," Progress in Neuro-Psychopharmacology & Biological Psychiatry, Mar. 2005, pp. 411-422, vol. 3.
Melissa J. Bain et al., "Predicting behavioral changes associated with age-related cognitive impairment in dogs," J Am Vet Med Assoc., Jun. 1, 2001, pp. 1,792-1,795, vol. 218, No. 11.
M.-A. Colle et al., "Vascular and parenchymal Abeta deposition in the aging dog: correlation with behavior," Neurobiol Aging, Sep. 2000, pp. 695-704, vol. 21.
Brian J. Cummings et al., "The Canine as an Animal Model of Human Aging and Dementia," Neurobiol Aging, Mar. 1996, pp. 259-268, vol. 17, No. 2.
Brian J. Cummings et al., "β-Amyloid Accumulation Correlates with Cognitive Dysfunction in the Aged Canine," Neurobiology of Learning and Memory, Jul. 1996, pp. 11-23, vol. 77.
Noah Dephoure et al., "Mapping and analysis of phosphorylation sites: a quick guide for cell biologists," Molecular Biology of the Cell, Mar. 1, 2013, vol. 24.
Chuong B. Do et al., "Protein Multiple Sequence Alignment," Methods in Molecular Biology, Feb. 2008, pp. 379-413, vol. 484.
Gholamreza Faridaalee et al., "Serum and Cerebrospinal Fluid Levels of S-100β Is A Biomarker for Spinal Cord Injury; a Systematic Review and Meta-Analysis, Archives of Academic Emergency Medicine," Arch Acad Emerg Med., Feb. 2019, vol. 7, No. 1.
Guy M. Mckhann et al., "The diagnosis of dementia due to Alzheimer's disease: recommendations from the National Institute on Aging-Alzheimer's Association workgroups on diagnostic guidelines for Alzheimer's disease," Alzheimers Dement., May 2011, pp. 263-269, vol. 7.
Julie A. Harris et al., "Many Neuronal and Behavioral Impairments in Transgenic Mouse Models of Alzheimer's Disease Are Independent of Caspase Cleavage of the Amyloid Precursor Protein," The Journal of Neuroscience, Jan. 6, 2010, pp. 372-381, vol. 30, No. 1.
E. Head et al, "Oxidative damage increases with age in a canine model of human brain aging," Journal of Neurochemistry, Jul. 2002, pp. 375-381, vol. 82.
Elizabeth Head, "A canine model of human aging and Alzheimer's disease," Biochimica et Biophysica Acta, Mar. 2013, pp. 1,384-1,389, vol. 1,832.
E. Head et al., "Spatial Learning and Memory as a Function of Age in the Dog," Behavioral Neuroscience, Oct. 1995, pp. 851-858, vol. 109, No. 5.
E. Head et al., "Visual-discrimination learning ability and beta-amyloid accumulation in the dog," Neurobiology of Aging, Sep. 1998, pp. 415-425, vol. 19, No. 5.
E. Head et al., "Region-specific age at onset of beta-amyloid in dogs," Neurobiology of Aging, Jan. 2000, pp. 89-96, vol. 21.
Elizabeth Head, "Combining an Antioxidant-Fortified Diet with Behavioral Enrichment Leads to Cognitive Improvement and Reduced Brain Pathology in Aging Canines," Ann N Y Acad Sci., Oct. 2007, pp. 398-406.
Y. Hou et al., "Distribution of β-amyloid in the canine brain," NeuroReport, Mar. 1997, pp. 1,009-1,012, vol. 8.
Albert Y. Hsia et al., "Plaque-independent disruption of neural circuits in Alzheimer's disease mouse models," Proc. Natl. Acad. Sci. USA, Mar. 1999, pp. 3,228-3,233, vol. 96.
D. Inekci et al., "Serum Fragments of Tau for the Differential Diagnosis of Alzheimer's Disease," Current Alzheimer Research, Jan. 2015, pp. 829-836, vol. 12.
E.M. Johnstone et al., "Conservation of the sequence of the Alzheimer's disease amyloid peptide in dog, polar bear and five other mammals by cross-species polymerase chain reaction analysis," Molecular Brain Research, Jul. 1991, pp. 299-305, vol. 10.
Kenneth M. Langa et al., "The Diagnosis and Management of Mild Cognitive Impairment: A Clinical Review," JAMA, Dec. 17, 2014, pp. 2,551-2,561, vol. 312, No. 23.
Gary Landsberg, "Therapeutic agents for the treatment of cognitive dysfunction syndrome in senior dogs," Progress in Neuro-Psychopharmacology & Biological Psychiatry, Feb. 16, 2005, vol. 29.
Noelia Lopez-Sanchez, "A Mutant Form of E2F4 Prevents Neuronal Tetraploidization and Cognitive Deficits in 5XFAD Mice Without Affecting Aβ Deposition," Alzheimer's and Dementia, Jul. 2017, pp. 659-661, vol. 13, No. 7.
Jose L. Luque-Garcia et al., "Sample preparation for serum/plasma profiling and biomarker identification by mass spectrometry," Journal of Chromatography A, Dec. 12, 2006, pp. 259-276, vol. 1,153.
Aladar Madari et al., "Assessment of severity and progression of canine cognitive dysfunction syndrome using the CAnine DEmentia Scale (CADES)," Applied Animal Behaviour Science, Oct. 2015, pp. 138-145, vol. 171.
Jere E. Meredith Jr. et al., "Characterization of Novel CSF Tau and ptau Biomarkers for Alzheimer's Disease," PLoS One, Oct. 2013, vol. 8, Issue 10.
N.W. Milgram et al., "Dietary enrichment counteracts age-associated cognitive dysfunction in canines," Neurobiology of Aging, Sep. 2002, pp. 737-745, vol. 23.
Sandra M. Morillo et al., "Nerve Growth Factor-Induced Cell Cycle Reentry in Newborn Neurons Is Triggered by p38MAPK-Dependent E2F4 Phosphorylation," Molecular and Cellular Biology, Jul. 2012, pp. 2,722-2,737, vol. 32, No. 14.
Momar Ndao, Biomarker Discovery in Serum/Plasma Using Surface Enhanced Laser Desorption Ionization Time of Flight (SELDI—TOF) Mass Spectrometry, Methods Mol Biol., Jan. 2012, pp. 67-79.
Jacqueline C. Neilson et al., "Prevalence of behavioral changes associated with age-related cognitive Impairment in dogs," JAVMA, Jun. 1, 2001, pp. 1,787-1,791, vol. 218, No. 11.
Wycliffe O. Opii et al., "Proteomic Identification of Brain Proteins in the Canine Model of Human Aging Following a Long-Term Treatment with Antioxidants and a Program of Behavioral Enrichment: Relevance to Alzheimer's Disease," Neurobiol Aging, Jan. 2008, pp. 51-70, vol. 29, No. 1.
Marco Pugliese et al., "Canine cognitive deficit correlates with diffuse plaque maturation and S100beta (−) astrocytosis but not with insulin cerebrospinal fluid level," Acta Neuropathol, Jun. 2006, pp. 519-528, vol. 111.
Reisa A. Sperling et al., "Toward defining the preclinical stages of Alzheimer's disease: Recommendations from the National Institute on Aging-Alzheimer's Association for workgroups on diagnostic guidelines for Alzheimer's disease," Alzheimer's & Dementia, May 2011, pp. 280-292, vol. 7.
J.E. Rofina et al., "Cognitive disturbances in old dogs suffering from the canine counterpart of Alzheimer's disease," Brain Research, Jan. 2006, pp. 216-226, vol. 1,069.
Michael J. Russell et al., "Familial influence on plaque formation in the beagle brain," NeuroReport, Dec. 1992, pp. 1,093-1,096, vol. 3, No. 12.
Manuel Sarasa et al., Natural Non-Trasgenic Animal Models for Research in Alzheimer's Disease, Current Alzheimer Research, Apr. 2009, pp. 171-178, vol. 6.
Takao Satou et al., "The progression of β-amyloid deposition in the frontal cortex of the aged canine," Brain Research, Nov. 1997, pp. 35-43, vol. 774.
Trine Schutt et al., "Dogs with Cognitive Dysfunction as a Spontaneous Model for Early Alzheimer's Disease: A Translational Study of Neuropathological and Inflammatory Markers," Journal of Alzheimer's Disease, Mar. 2016, pp. 133-449, vol. 52.
V.A. Simossis et al., "Integrating Protein Secondary Structure Prediction and Multiple Sequence Alignment," Current Protein and Peptide Science, Aug. 2004, pp. 249-266, vol. 5.
Christina T. Siwak et al., "Comparison of the effects of adrafinil, propentofylline, and nicergoline on behavior in aged dogs," AJVR, Nov. 2000, pp. 1,410-1,414, vol. 61, No. 11.
Christina T. Siwak et al., "Effect of Age and Level of Cognitive Function on Spontaneous and Exploratory Behaviors in the Beagle Dog," Learning & Memory, Nov. 2001, pp. 317-325, vol. 8, No. 6.

(56) References Cited

OTHER PUBLICATIONS

Christina T. Siwak et al., "Chronic antioxidant and mitochondrial cofactor administration improves discrimination learning in aged but not young dogs," Progress in Neuro-Psychopharmacology & Biological Psychiatry, Mar. 2005, pp. 461-469, vol. 29.

Christina T. Siwak-Tapp et al., "Region specific neuron loss in the aged canine hippocampus is reduced by enrichment," Neurobiol Aging, Jan. 2008, pp. 39-50, vol. 29, No. 1.

Binggui Sun et al., "Cystatin C—Cathepsin B Axis Regulates Amyloid Beta Levels and Associated Neuronal Deficits in an Animal Model of Alzheimer's Disease," Neuron., Oct. 23, 2008, pp. 247-257, vol. 60, No. 2.

P. Dwight Tapp et al., "Effects of Age on Measures of Complex Working Memory Span in the Beagle Dog (Canis familiaris) Using Two Versions of a Spatial List Learning Paradigm," Learning & Memory, Mar. 2003, pp. 148-160, vol. 10.

Fabrizio Trinchese et al., "Progressive Age-Related Development of Alzheimer-like Pathology in APP/PS1 Mice," Ann Neurol, Jun. 2004, pp. 801-814, vol. 55.

Jerzy Wegiel et al., "Subpopulation of dogs with severe brain parenchymal 13 amyloidosis distinguished with cluster analysis," Brain Research, Jul. 1996, pp. 20-26, vol. 728.

T. Yoshino et al., "A Retrospective Study of Canine Senile Plaques and Cerebral Amyloid Angiopathy," Vet Pathol, Mar. 1996, pp. 230-234, vol. 33.

METHOD FOR DETERMINING THE RISK OF DEVELOPING ALZHEIMER'S DISEASE

FIELD OF THE INVENTION

The present invention relates to methods for determining the risk of developing Alzheimer, for designing a personalized therapy and for selecting patients.

BACKGROUND OF THE INVENTION

Alzheimer's disease (AD) is one of the most prevalent neurodegenerative disorders in Western societies. To date, there are no known therapies that stop this condition, and most clinical trials which have been designed to date aimed at inhibiting beta-amyloid peptide or hyperphosphorylated tau protein production and/or activity. Due to the failure of the clinical trials conducted to date, particularly the failure to obtain any cognitive improvement after treatment with solanezumab and bapineuzumab antibodies, the need to move these treatments forward to early phases of the disease before the neurodegenerative process becomes irreversible has been considered.

This type of approach is being carried out today in patients with familial Alzheimer's, a rare form of Alzheimer's which is characterized by the existence of mutations accelerating the neurodegenerative process. Nevertheless, the highest percentage of patients suffers from sporadic Alzheimer's, a type of pathology which is not predictable as of today.

Biomarkers that have been described to date are mainly based on neuroimaging techniques (e.g., senile plaque density and atrophy quantification in different regions of the brain, brain glucose metabolism analysis) and techniques for the quantification of soluble β-amyloid and tau forms in the cerebrospinal fluid or blood serum of patients (Kang et al., 2014 *Korean J Physiol Pharmacol.* 18: 447-456). All these techniques are therefore based on analyzing late products of the pathology.

There is therefore a need to identify non-invasive early markers of Alzheimer's which allow making the diagnosis in the earliest possible stage of the disease, and therefore determining the risk of developing Alzheimer.

BRIEF DESCRIPTION OF THE INVENTION

In a first aspect, the invention relates to an in vitro method for determining the risk of developing Alzheimer's disease or a cognitive disorder similar to said disease in a subject, which method comprises
 a) determining in a sample from the subject the level of phosphorylation in threonine residues in E2F4 protein or in a functionally equivalent variant and
 b) comparing the level of phosphorylation obtained in a) to a reference value,
wherein an increase in the level of phosphorylation in threonine residues in E2F4 protein or in a functionally equivalent variant compared to a reference value is indicative that said subject has a high risk of developing Alzheimer's or a cognitive disorder similar to said disease.

In a second aspect, the invention relates to an in vitro method for designing a personalized therapy in a subject suffering from mild cognitive impairment, which method comprises
 a) determining in a sample from the subject the level of phosphorylation in threonine residues in E2F4 protein or in a functionally equivalent variant and
 b) comparing the level of phosphorylation obtained in a) to a reference value,
wherein an increase in the level of phosphorylation in threonine residues in E2F4 protein or in a functionally equivalent variant compared to the reference value is indicative that said subject is susceptible to receive a therapy for the prevention and/or treatment of Alzheimer's disease or a cognitive disorder similar to said disease.

In a third aspect, the invention relates to an in vitro method for selecting a patient susceptible to be treated with a therapy for the prevention and/or treatment of Alzheimer's or a cognitive disorder similar to said disease, which method comprises
 a) determining in a sample from the subject the level of phosphorylation in threonine residues in E2F4 protein or in a functionally equivalent variant and
 b) comparing the level of phosphorylation obtained in a) to a reference value,
wherein an increase in the level of phosphorylation in threonine residues in E2F4 protein or in a functionally equivalent variant compared to the reference value is indicative that said subject is a candidate for receiving a therapy for the prevention and/or treatment of Alzheimer's disease or a cognitive disorder similar to said disease.

In a fourth aspect, the invention relates to the use of E2F4 or a functionally equivalent variant thereof, wherein the E2F4 or variant is phosphorylated in threonine as a marker of the risk of developing Alzheimer's disease or a cognitive disorder similar to Alzheimer's disease.

In a fifth aspect, the invention relates to a kit comprising a reagent capable of determining the level of phosphorylation in threonine residues of E2F4 protein for determining the risk of a subject developing Alzheimer's or a cognitive disorder similar to Alzheimer's disease, for designing a personalized therapy in a subject or for selecting a patient susceptible to be treated with a therapy for the prevention and/or treatment of Alzheimer's disease or a cognitive disorder similar to Alzheimer's disease.

In a sixth aspect, the invention relates to the use of a kit according to the invention for determining the risk of a subject developing Alzheimer's disease or a cognitive disorder similar to said disease in a subject, for designing a personalized therapy in a subject suffering from mild cognitive impairment or for selecting a patient susceptible to be treated with a therapy for the prevention and/or treatment of Alzheimer's or a cognitive disorder similar to said disease.

DETAILED DESCRIPTION

Figure 1:
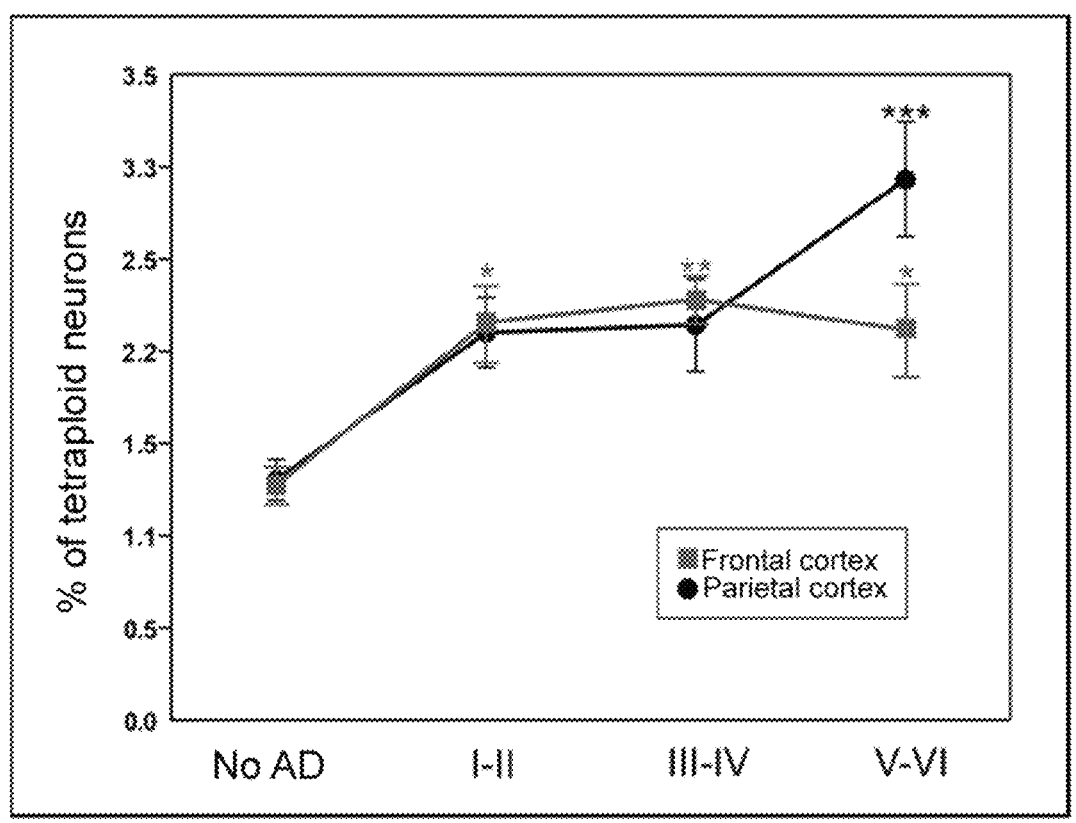
FIG. 1 shows levels of neuronal tetraploidy in human frontal and parietal cortex, estimated by means of flow cytometry in fresh cell nuclei that are positive for the neuron-specific NeuN antigen. An increase in the percentage of tetraploid neurons prior to the presence of neurofibrillary tangles, which are not detected in the neocortex until Braak Stages V-VI, the final stage of the pathology where the patients exhibit symptoms of AD, is observed. *$p<0.05$; $p<0.01$; *$p<0.005$ (Student's t-test).

The inventors of the present invention have identified the transcription factor, E2F4, phosphorylated in threonine residues as a biomarker for the early stages of Alzheimer's disease, and said marker therefore allows predicting the development of Alzheimer's disease or a cognitive disorder similar to said disease.

Methods of the Invention

In a first aspect, the invention relates to an in vitro method for determining the risk of developing Alzheimer's disease or a cognitive disorder similar to said disease in a subject (first method of the invention), which method comprises
 a) determining in a sample from the subject the level of phosphorylation in threonine residues in E2F4 protein or in a functionally equivalent variant and
 b) comparing the level of phosphorylation obtained in a) to a reference value,
wherein an increase in the level of phosphorylation in threonine residues in E2F4 protein or in a functionally equivalent variant compared to a reference value is indicative that said subject has a high risk of developing Alzheimer's or a cognitive disorder similar to said disease.

In a particular embodiment, the subject suffers from mild cognitive impairment.

As it is used herein, "mild cognitive impairment", also known as incipient dementia or isolated cognitive impairment, refers to a nosologic entity that seeks to describe the symptomatology before the onset of dementia. Affected individuals suffer from impairments that are more advanced than expected for their age and level of education, but these impairments do not significantly interfere with their daily activities. It is considered as the limit between normal aging and dementia.

The person skilled in the art is capable of identifying if a subject has a mild cognitive impairment based, for example, on the diagnostic criteria set forth in the Diagnostic and Statistical Manual of Mental Disorders (DSM) and in the International Classification of Diseases, which allow physicians to make their diagnoses.

In a particular embodiment of the first method of the invention, the subject is a human and the neurodegenerative disease is Alzheimer's disease, or the subject is a dog and the cognitive disorder similar to Alzheimer's disease is cognitive dysfunction syndrome.

As it is used herein, the expression "risk of developing Alzheimer's disease or a cognitive disorder similar to said disease" refers to the predisposition, susceptibility, propensity or likelihood of a subject developing Alzheimer's disease or a cognitive disorder similar to said disease. The risk of developing a neurodegenerative disease, Alzheimer's disease or a cognitive disorder similar to said disease generally means that there is a high or low risk or a higher or lower risk. Therefore, a subject with a high risk of developing Alzheimer's disease or a cognitive disorder similar to said disease has a likelihood of developing said disease of at least 50%, or at least 60%, or at least 70%, or at least 80%, or at least 90%, or at least 95%, or at least 97%, or at least 98%, or at least 99%, or at least 100%. Similarly, a subject with a low risk of developing Alzheimer's disease or a cognitive disorder similar to said disease is a subject having at least a likelihood of developing said disease of at least 0%, or at least 1%, or at least 2%, or at least 3%, or at least 5%, or at least 10%, or at least 20%, or at least 30%, or at least 40%, or at least 49%.

In general, the expression "predicting the risk", "prediction of the risk" or the like, refers to the risk of a patient developing Alzheimer's disease or a cognitive disorder similar to said disease, whether it is high or low. As will be understood by those skilled in the art, although the prediction (or risk) is preferable, it does not have to be correct for all the subjects to be evaluated, although it is preferable for it to be so. The term, however, requires a statistically significant part of the subjects being identified as exhibiting a higher likelihood of having a specific result. The person skilled in the art can determine without much difficulty if a part is statistically significant using different, well-known statistical evaluation tools, for example, the determination of confidence intervals, determination of p-value, cross-validation with classification indices, etc. Preferred confidence intervals are at least 50%, at least 60%, at least 70%, at least 80%, at least 90% or at least 95%. p-values are preferably 0.1, 0.05, 0.02, 0.01 or less.

The term "Alzheimer's disease or AD" refers to a mental impairment associated with a specific degenerative brain disease which is characterized by the appearance of senile plaques, neurofibrillary tangles and progressive neuronal loss clinically manifested as progressive memory deficiencies, confusion, behavioral problems, inability to take care of oneself, gradual physical deterioration, and ultimately death. In preferred embodiments, Alzheimer's disease is a disease in any of the stages according to the Braak scale:
 Stages I-II: the brain area affected by the presence of neurofibrillary tangles corresponds to the transentorhinal region of the brain
 Stages the affected brain area also extends to areas of the limbic region, such as the hippocampus
 Stages V-VI: the affected brain area also involves the neocortical region.

This classification by neuropathological stages is correlated with the clinical progression of the disease, there being parallelism between memory decline with neurofibrillary changes and the formation of neuritic plaques in the entorhinal cortex and hippocampus (stages I to IV). Likewise, the isocortical presence of these changes (stages V and VI) is correlated with clinically severe alterations. The transentorhinal stage (I-II) corresponds to clinically silent periods of the disease. The limbic stage (III-IV) corresponds to a clinically incipient AD. The neocortical stage corresponds to a fully developed AD.

As it is used herein, "cognitive dysfunction syndrome or SDC" refers to a syndrome that any pet can have and corresponds to a state of dementia in which the cognitive process is compromised, which can occur with motor or sensorial symptomatology or veterinary problems. Cognitive dysfunction syndrome (CDS) in dogs is an age-associated neurodegenerative disorder which is characterized by a decline in brain functions. Like Alzheimer's disease, extracellular beta-amyloid (PBA) protein deposits, but not intracellular tau protein deposits, are produced. This PBA deposit is the final result of extreme oxidative stress and greater formation of insoluble forms of PBA 1-42, which are determined by genetic and environmental interaction.

In a second aspect, the invention relates to an in vitro method for designing a personalized therapy in a subject suffering from mild cognitive impairment (second method of the invention), which method comprises
a) determining in a sample from the subject the level of phosphorylation in threonine residues in E2F4 protein or in a functionally equivalent variant and
b) comparing the level of phosphorylation obtained in a) to a reference value,
wherein an increase in the level of phosphorylation in threonine residues in E2F4 protein or in a functionally equivalent variant compared to the reference value is indicative that said subject is susceptible to receive a therapy for the prevention and/or treatment of Alzheimer's disease or a cognitive disorder similar to said disease.

In a particular embodiment of the second method of the invention, the subject is a human and the therapy is for the prevention and/or treatment of Alzheimer's disease, or the subject is a dog and the therapy is for the prevention and/or treatment of cognitive dysfunction syndrome.

As it is used herein, the term "preventive therapy" refers to the prevention of or a set of prophylactic measures for preventing a disease to prevent or delay the onset of the symptomatology of the disease. Particularly, said term refers to the prevention of or the set of measures for preventing the onset or delaying the clinical symptomatology associated with Alzheimer's disease or a cognitive disorder similar to said disease. Desired clinical results associated with the administration of said treatment to a subject include, but are not limited to, stabilizing the pathological state of the disease, delaying the progression of the disease or improving the physiological state of the subject.

As it is used herein, "therapy for the treatment" refers to the tentative recovery of a health issue, generally after a diagnosis, specifically of Alzheimer's disease or a cognitive disorder similar to said disease. So it is not necessarily a cure, i.e., a complete reversion of a disease. Therefore, as it is used herein "treatment" covers any treatment of a disease, a disorder or a condition of a mammal, particularly a human being, and includes inhibiting the disease or condition, i.e., stopping its development; or alleviating the disease or condition, i.e., causing the regression of the disease or condition or improving one or more symptoms of the disease or condition. The population of subjects treated by means of the method includes a subject suffering from the unwanted condition or disease, as well as subjects at risk of developing the condition or disease. Therefore, a person skilled in the art understands that a treatment can improve the condition of the patient, but it may not be a complete cure for the disease.

Preventive or curative treatments suitable in Alzheimer's disease or in a cognitive disorder similar to said disease include, but are not limited to, choline-esterase inhibitors such as, for example, donepezil hydrochloride (Aricept), rivastigmine (Exelon) and galantamine (Reminyl), N-methyl D-aspartate (NMDA) receptor antagonists, or monoclonal antibodies such as solanezumab and bapineuzumab.

In a third aspect, the invention relates to an in vitro method for selecting a patient susceptible to be treated with a therapy for the prevention and/or treatment of Alzheimer's or a cognitive disorder similar to said disease (third method of the invention), which method comprises
a) determining in a sample from the subject the level of phosphorylation in threonine residues in E2F4 protein or in a functionally equivalent variant and
b) comparing the level of phosphorylation obtained in a) to a reference value,
wherein an increase in the level of phosphorylation in threonine residues in E2F4 protein or in a functionally equivalent variant compared to the reference value is indicative that said subject is a candidate for receiving a therapy for the prevention and/or treatment of Alzheimer's disease or a cognitive disorder similar to said disease.

As it is used herein, the term "select" refers to the action of choosing a subject to put said subject under a preventive or curative treatment for Alzheimer's disease or a cognitive disorder similar to said disease.

In a particular embodiment of the third method of the invention, the subject is a human and the therapy is for the prevention and/or treatment of Alzheimer's disease, or the subject is a dog and the therapy is for the prevention and/or treatment of cognitive dysfunction syndrome.

The first, second and third methods of the invention comprise in a first step determining in a sample from a subject the level of phosphorylation in threonine residues in E2F4 protein or in a functionally equivalent variant.

As it is used herein, "sample" refers to the biological material isolated from a subject. The sample can be isolated from any suitable biological fluid or tissue including, by way of illustrative and non-limiting example, cerebrospinal fluid, blood serum, blood plasma, tears, sweat, saliva, urine and feces.

In a particular embodiment of the methods of the invention, the sample is selected from the group consisting of cerebrospinal fluid, blood serum, blood plasma, blood and peripheral blood mononuclear cells.

As it is used herein, the term "subject" refers to a member of a mammalian animal species and includes, but is not limited to, domestic animals, primates and humans. In a particular embodiment, the subject is preferably a male or female human being of any age or race. In another particular embodiment, the subject is a dog. In a more particular embodiment, the subject suffers from mild cognitive impairment.

Human "E2F4" protein corresponds with the protein identified in the Uniprot database as Q16254 (27 May 2015). E2F4 protein in dogs corresponds with the protein identified in the Uniprot database as J9NSJ4 (27 May 2015) and the isoform thereof identified in the Uniprot database as F1P6Y0 (1 Apr. 2015).

In the context of the present invention, the term "functionally equivalent variant of E2F4 protein" includes (i) variants of E2F4 protein in which one or more of the amino acid residues are substituted with a conserved or non-conserved amino acid residue (preferably a conserved amino acid residue), wherein such substituted amino acid residue may or may be not be a residue encoded by the genetic code, as well as (ii) variants comprising an insertion or a deletion of one or more amino acids and playing the same function as E2F4 protein, i.e., capable of inhibiting the expression of genes, specifically genes involved in DNA replication and cell cycle regulation.

The variants according to the invention preferably have a sequence identity with the E2F4 amino acid sequence of at least 50%, at least 60%, at least 70%, at least 80%, at least 90%, at least 91%, at least 92%, at least 93%, at least 94%, at least 95%, at least 96%, at least 97%, at least 98% or at least 99%. The degree of identity between the variants and the specific sequences of E2F4 protein defined above can be determined using algorithms and computational methods that are well-known for those skilled in the art. The identity between two amino acid sequences is preferably determined using the BLASTP algorithm [BLAST Manual, Altschul, S., et. al., NCBI NLM NIH Bethesda, Md. 20894, Altschul, S., et. al., J. Mol. Biol. 215: 403-410 (1990)].

The degree of phosphorylation of a protein can be determined using any conventional method known by those skilled in the art. Various assays are known for determining the state of phosphorylation of a protein, or the amino acid residue which is phosphorylated in a specific protein, such as, for example, in vitro kinase activity assays using radioactively labeled ATP; two-dimensional electrophoresis of proteins thus phosphorylated and labeled (which allows analyzing how many amino acid residues are phosphorylated in a protein); mass spectrometry of the previously purified protein the state of phosphorylation of which is to be measured; directed mutagenesis followed by the in vitro kinase activity assay with the purified proteins; phosphopeptide analysis which involves separating a phosphorylated protein into two dimensions after trypsin digestion, or the less technically complicated Western blot, which contemplates using antibodies against said protein specifically recognizing the amino acid residue or epitope of the protein which is phosphorylated. Techniques for detecting phosphorylated residues in proteins are well-known by the person skilled in the art and are described in the state of the art. Alternatively, E2F4 protein can be immunoprecipitated and the total level of phosphorylation in threonines or in the threonine residues of interest can be determined by means of Western Blot.

In a preferred embodiment, the determination of the phosphorylation is carried out by means of the ELISA technique.

The immunoassay known as ELISA is based on the use of enzyme-labeled antibodies or antigens, such that the conjugates formed between the target antigen and the labeled antibody results in the formation of enzymatically active complexes. Due to the fact that one of the components (the labeled antibody or antigen) is immobilized on a support, the antibody-antigen complexes are immobilized on the support and can therefore be detected by the addition of a substrate which is converted by the enzyme into a product that is detectable by spectrophotometry or fluorometry, for example. Preferably, the ELISA assay used in the methods of the present invention is a sandwich ELISA assay, wherein a first antibody (capture antibody) which is adsorbed on a solid support and is specific for the antigen to be detected, which would allow capturing the antigen to be detected on said support, is used. The sandwich ELISA assay requires using a second antibody (detection antibody) which is also specific for the antigen to be detected and is added to the previously formed complexes between the antigen and the capture antibody.

As it is used herein, the term "antibody" seeks to include both chimeric or recombinant antibodies and monoclonal antibodies and polyclonal antibodies or proteolytic fragments thereof, such as Fab or F(ab') 2 fragments, etc. Furthermore, the DNA encoding the variable region of the antibody can be inserted in other antibodies to thereby produce chimeric antibodies. Single-chain antibodies (scFv) can be polypeptides formed by single chains having the characteristic capacity of an antigen-binding antibody and comprising a pair of amino acid sequences homologous or analogous to the variables regions of the light and heavy chains of immunoglobulins (VH-VL or scFv binding). Polypeptides analogous to the variable regions of the light and heavy chains of an antibody can bind, if desired, through a binding polypeptide. Methods for producing antibodies are well-known and described in the state of the art.

As will be understood by the person skilled in the art, given that the level of phosphorylation in threonine residues of E2F4 protein or a functionally equivalent variant is to be determined, the ELISA assay can be carried out by means of a sandwich-type ELISA assay, wherein the capture antibody is an antibody specific against E2F4 protein, and wherein the detection antibody is an antibody specific against phosphothreonine or against specific phosphothreonine residues present in E2F4 protein. Alternatively, a sandwich ELISA assay can be carried out using an anti-phosphothreonine antibody or an antibody specific against one or more specific phosphothreonine residues as a capture antibody, for the purpose of immobilizing all those proteins with phosphorylation in phosphothreonine residues, and an anti-E2F4 antibody as a detection antibody.

As will be understood by the person skilled in the art, given that the level of phosphorylation in threonine residues of E2F4 protein or a functionally equivalent variant is to be determined, it is recommendable to quantify the overall levels of E2F4 protein such that the values of E2F4 phosphorylated in threonine can be normalized. The levels of E2F4 can be determined, for example, by means using an antibody recognizing E2F4, such as those commercially available antibodies. Additionally, given that the level of phosphorylation of E2F4 protein is to be determined, it is recommendable to include phosphatase inhibitors in the assays, such that the levels of phosphorylation are not altered.

In a particular embodiment of the methods of the invention, the first step comprises determining the phosphorylation of the threonine residue selected from the group consisting of the threonine residue in position 248 (Thr248), threonine residue in position 250 (Thr250), threonine residue in position 14 (Thr14), threonine residue in position 163 (Thr163), threonine residue in position 224 (Thr224) and threonine residue in position 333 (Thr333), and combinations thereof, of human E2F4 protein, or in a phosphorylatable, positionally equivalent amino acid residue of another E2F4 protein as defined by multiple amino acid sequence alignment or in a functionally equivalent variant.

As it is used herein, the term "positionally equivalent" refers to the position of an amino acid of an E2F4 protein which, by means of multiple amino acid sequence alignment of E2F4 protein, corresponds to Thr248, Thr250, Thr14, Thr163, Thr224 and/or Thr333 of human E2F4 protein.

Multiple sequence alignment can be carried out by means of the algorithm implemented in the CLUSTALW2 program (using standard parameters (alignment type: slow; matrix: Gonnet; gap open: 10; gap extension: 0.1; KTUP: 1; Window length: 5; Score type: percent; Top Diags: 5 and Pair Gap: 3). In another embodiment, multiple sequence alignment can be carried out by means of the algorithm implemented in the CLUSTAL OMEGA program using standard parameters (HHalign algorithm with default parameters and the default transition matrix is Gonnet, with a 6-bit gap opening penalty and a 1-bit gap extension).

In another more particular embodiment, the methods of the invention comprise determining the phosphorylation of one or more threonine residues of human E2F4 protein, namely Thr248, Thr250, Thr14, Thr163, Thr224 and/or Thr333, or in one or more phosphorylatable, positionally equivalent amino acid residues of another E2F4 protein as defined by multiple amino acid sequence alignment or in a functionally equivalent variant.

In a more particular embodiment, the methods of the invention comprise determining the phosphorylation of only one of the threonine residues selected from the group consisting of Thr248, Thr250, Thr14, Thr163, Thr224 and Thr333 of human E2F4 protein, or in a phosphorylatable, positionally equivalent amino acid residue of another E2F4 protein as defined by multiple amino acid sequence alignment or in a functionally equivalent variant In another embodiment, the methods of the invention comprise determining the phosphorylation of two threonine residues selected from the group consisting of Thr248 and Thr250; Thr248 and Thr14; Thr248 and Thr163; Thr248 and Thr224; Thr248 and Thr333; Thr250 and Thr14; Thr250 and Thr163; Thr250 and Thr224; Thr250 and Thr333; Thr14 and Thr163; Thr14 and Thr224; Thr14 and Thr333; Thr163 and Thr224; Thr163 and Thr333; and Thr224 and Thr333 of human E2F4 protein, or in two phosphorylatable, positionally equivalent amino acid residues of another E2F4 protein as defined by multiple amino acid sequence alignment or in a functionally equivalent variant.

In another embodiment, the methods of the invention comprise determining the phosphorylation of three threonine residues selected from the group consisting of Thr248, Thr250 and Thr14; Thr248, Thr250 and Thr163; Thr248, Thr250 and Thr224; Thr248, Thr250 and Thr333; Thr248, Thr14 and Thr163; Thr248, Thr14 and Thr224; Thr248, Thr14 and Thr333; Thr248, Thr163 and Thr224; Thr248, Thr163 and Thr333; Thr248, Thr224 and Thr333; Thr250, Thr14 and Thr163; Thr250, Thr14 and Thr224; Thr250, Thr14 and Thr333; Thr250, Thr163 and Thr224; Thr250, Thr163 and Thr333; Thr250, Thr224 and Thr333; Thr14, Thr163 and Thr224; Thr14, Thr163 and Thr333; Thr14, Thr224 and Thr333; and Thr163, Thr224 and Thr333 of human E2F4 protein, or in three phosphorylatable, positionally equivalent amino acid residues of another E2F4 protein as defined by multiple amino acid sequence alignment or in a functionally equivalent variant.

In another embodiment, the methods of the invention comprise determining the phosphorylation of four threonine residues selected from the group consisting of Thr248, Thr250, Thr14 and Thr163; Thr248, Thr250, Thr14 and Thr224; Thr248, Thr250, Thr14 and Thr333; Thr248, Thr250, Thr163 and Thr224; Thr248, Thr250, Thr163 and Thr333; Thr248, Thr250, Thr224 and Thr333; Thr248, Thr14, Thr163 and Thr224; Thr248, Thr14, Thr163 and Thr333; Thr248, Thr14, Thr224 and Thr333; Thr248, Thr163, Thr224 and Thr333; Thr250, Thr14, Thr163 and Thr224; Thr250, Thr14, Thr163 and Thr333; Thr250, Thr14, Thr224 and Thr333; Thr250, Thr163, Thr224 and Thr333; and Thr14, Thr163, Thr224 and Thr333 of human E2F4 protein, or in four phosphorylatable, positionally equivalent amino acid residues of another E2F4 protein as defined by multiple amino acid sequence alignment or in a functionally equivalent variant.

In another embodiment, the methods of the invention comprise determining the phosphorylation of five threonine residues selected from the group consisting of Thr248, Thr250, Thr14, Thr163 and Thr224; Thr248, Thr250, Thr14, Thr163 and Thr333; Thr248, Thr250, Thr14, Thr224 and Thr333; Thr248, Thr250, Thr163, Thr224 and Thr333; Thr248, Thr14, Thr163, Thr224 and Thr333; and Thr250, Thr14, Thr163, Thr224 and Thr333 of human E2F4 protein, or in five phosphorylatable, positionally equivalent amino acid residues of another E2F4 protein as defined by multiple amino acid sequence alignment or in a functionally equivalent variant.

In another embodiment, the methods of the invention comprise determining the phosphorylation of six threonine residues, namely Thr248, Thr250, Thr14, Thr163, Thr224 and Thr333 of human E2F4 protein, or in six phosphorylatable, positionally equivalent amino acid residues of another E2F4 protein as defined by multiple amino acid sequence alignment or in a functionally equivalent variant.

In another embodiment, the methods of the invention comprise determining the phosphorylation in threonine of human E2F4 protein as detected by means of using anti-phosphothreonine antibodies.

In another embodiment, the methods of the invention comprise determining the mean phosphorylation in threonine residues of human E2F4 protein. By way of illustration, this determination can be carried out by means of isolating human E2F4, for example, by means of using human anti-E2F4 antibodies, followed by quantitative or semi-quantitative immunodetection using antibodies specific against phosphothreonine to that end.

In a particular embodiment of the methods of the invention, the subject is a dog and phosphorylation is determined for the threonine residue selected from the group consisting of threonine in position 311 (Thr311), threonine in position 313 (Thr313), threonine in position 76 (Thr76), threonine in position 225 (Thr225), threonine in position 286 (Thr286), threonine in position 391 (Thr391), threonine in position 40 (Thr40) and combinations thereof of dog E2F4 protein with Uniprot database accession number J9NSJ4, or in a phosphorylatable, positionally equivalent amino acid residue of another E2F4 protein as defined by multiple amino acid sequence alignment or in a functionally equivalent variant.

In another more particular embodiment, the methods of the invention comprise determining phosphorylation of one or more threonine residues of dog E2F4 protein with Uniprot database accession number J9NSJ4, namely Thr311, Thr313, Thr76, Thr225, Thr286, Thr391 and Thr40, or in one or more phosphorylatable, positionally equivalent amino acid residues of another E2F4 protein as defined by multiple amino acid sequence alignment or in a functionally equivalent variant.

In a more particular embodiment, the methods of the invention comprise determining the phosphorylation of only one of the threonine residues selected from the group consisting of Thr311, Thr313, Thr76, Thr225, Thr286, Thr391 and Thr40 of dog E2F4 with Uniprot database accession number J9NSJ4, or in a phosphorylatable, positionally equivalent amino acid residue of another E2F4 protein as defined by multiple amino acid sequence alignment or in a functionally equivalent variant.

In another embodiment, the methods of the invention comprise determining the phosphorylation of two threonine residues selected from the group consisting of Thr311 and Thr313; Thr311 and Thr76; Thr311 and Thr225; Thr311 and Thr286; Thr311 and Thr391; Thr311 and Thr40; Thr313 and Thr76; Thr313 and Thr225; Thr313 and Thr286; Thr313 and Thr391; Thr313 and Thr40; Thr76 and Thr225; Thr76 and Thr286; Thr76 and Thr391; Thr76 and Thr40; Thr225 and Thr286; Thr225 and Thr391; Thr225 and Thr40; Thr286 and Thr391; Thr286 and Thr40; and Thr391 and Thr40 of dog E2F4 protein with Uniprot database accession number J9NSJ4, or in two phosphorylatable, positionally equivalent amino acid residues of another E2F4 protein as defined by multiple amino acid sequence alignment or in a functionally equivalent variant.

In another embodiment, the methods of the invention comprise determining the phosphorylation of three threonine residues selected from the group consisting of Thr311, Thr313 and Thr76; Thr311, Thr313 and Thr225; Thr311, Thr313 and Thr286; Thr311, Thr313 and Thr391; Thr311, Thr313 and Thr40; Thr311, Thr76 and Thr225; Thr311, Thr76 and Thr286; Thr311, Thr76 and Thr391; Thr311, Thr76 and Thr40; Thr311, Thr225 and Thr286; Thr311, Thr225 and Thr391; Thr311, Thr225 and Thr40; Thr311, Thr286 and Thr391; Thr311, Thr286 and Thr40; Thr311, Thr391 and Thr40; Thr313, Thr76 and Thr225; Thr313, Thr76 and Thr286; Thr313, Thr76 and Thr391; Thr313, Thr76 and Thr40; Thr313, Thr225 and Thr286; Thr313, Thr225 and Thr391; Thr313, Thr225 and Thr40; Thr313, Thr286 and Thr391; Thr313, Thr286 and Thr40; Thr313, Thr391 and Thr40; Thr76, Thr225 and Thr286; Thr76, Thr225 and Thr391; Thr76, Thr225 and Thr40; Thr76, Thr286 and Thr391; Thr76, Thr286 and Thr40; Thr76, Thr391 and Thr40; Thr225, Thr286 and Thr391; Thr225, Thr286 and Thr40; Thr225, Thr391 and Thr40; and Thr286, Thr391 and Thr40 of dog E2F4 protein with Uniprot database accession number J9NSJ4, or in three phosphorylatable, positionally equivalent amino acid residues of another E2F4 protein as defined by multiple amino acid sequence alignment or in a functionally equivalent variant.

In another embodiment, the methods of the invention comprise determining the phosphorylation of four threonine residues selected from the group consisting of Thr311, Thr313, Thr76 and Thr225; Thr311, Thr313, Thr76 and Thr286; Thr311, Thr313, Thr76 and Thr391; Thr311, Thr313, Thr76 and Thr40; Thr311, Thr313, Thr225 and Thr286; Thr311, Thr313, Thr225 and Thr391; Thr311, Thr313, Thr225 and Thr40; Thr311, Thr313, Thr286 and Thr391; Thr311, Thr313, Thr286 and Thr40; Thr311, Thr313, Thr391 and Thr40; Thr311, Thr76, Thr225 and Thr286; Thr311, Thr76, Thr225 and Thr391; Thr311, Thr76, Thr225 and Thr40; Thr311, Thr76, Thr286 and Thr391; Thr311, Thr76, Thr286 and Thr40; Thr311, Thr76, Thr391 and Thr40; Thr311, Thr225, Thr286 and Thr391; Thr311, Thr225, Thr286 and Thr40; Thr311, Thr225, Thr391 and Thr40; Thr311, Thr286, Thr391 and Thr40; Thr313, Thr76, Thr225 and Thr286; Thr313, Thr76, Thr225 and Thr391; Thr313, Thr76, Thr225 and Thr40; Thr313, Thr76, Thr286 and Thr391; Thr313, Thr76, Thr286 and Thr40; Thr313, Thr76, Thr391 and Thr40; Thr313, Thr225, Thr286 and Thr391; Thr313, Thr225, Thr286 and Thr40; Thr313, Thr225, Thr391 and Thr40; Thr313, Thr286, Thr391 and Thr40; Thr76, Thr225, Thr286 and Thr391; Thr76, Thr225, Thr286 and Thr40; Thr76, Thr225, Thr391 and Thr40; Thr76, Thr286, Thr391 and Thr40; and Thr225, Thr286, Thr391 and Thr40 of dog E2F4 protein with Uniprot database accession number J9NSJ4, or in four phosphorylatable, positionally equivalent amino acid residues of another E2F4 protein as defined by multiple amino acid sequence alignment or in a functionally equivalent variant.

In another embodiment, the methods of the invention comprise determining the phosphorylation of five threonine residues selected from the group consisting of Thr311, Thr313, Thr76, Thr225 and Thr286; Thr311, Thr313, Thr76, Thr225 and Thr391; Thr311, Thr313, Thr76, Thr225 and Thr40; Thr311, Thr313, Thr76, Thr286 and Thr391; Thr311, Thr313, Thr76, Thr286 and Thr40; Thr311, Thr313, Thr76, Thr391 and Thr40; Thr311, Thr313, Thr225, Thr286 and Thr391; Thr311, Thr313, Thr225, Thr286 and Thr40; Thr311, Thr313, Thr225, Thr391 and Thr40; Thr311, Thr313, Thr286, Thr391 and Thr40; Thr311, Thr76, Thr225, Thr286 and Thr391; Thr311, Thr76, Thr225, Thr286 and Thr40; Thr311, Thr76, Thr225, Thr391 and Thr40; Thr311, Thr76, Thr286, Thr391 and Thr40; Thr311, Thr225, Thr286, Thr391 and Thr40; Thr313, Thr76, Thr225, Thr286 and Thr391; Thr313, Thr76, Thr225, Thr286 and Thr40; Thr313, Thr76, Thr225, Thr391 and Thr40; Thr313, Thr76, Thr286, Thr391 and Thr40; Thr313, Thr225, Thr286, Thr391 and Thr40; and Thr76, Thr225, Thr286, Thr391 and Thr40 of dog E2F4 protein with Uniprot database accession number J9NSJ4, or in five phosphorylatable, positionally equivalent amino acid residues of another E2F4 protein as defined by multiple amino acid sequence alignment or in a functionally equivalent variant.

In another embodiment, the methods of the invention comprise determining the phosphorylation of six threonine residues selected from the group consisting of Thr311, Thr313, Thr76, Thr225, Thr286 and Thr391; Thr311, Thr313, Thr76, Thr225, Thr286 and Thr40; Thr311, Thr313, Thr76, Thr225, Thr391 and Thr40; Thr311, Thr313, Thr76, Thr286, Thr391 and Thr40; Thr311, Thr313, Thr225, Thr286, Thr391 and Thr40; Thr311, Thr76, Thr225, Thr286, Thr391 and Thr40; and Thr313, Thr76, Thr225, Thr286, Thr391 and Thr40 of dog E2F4 protein with Uniprot database accession number J9NSJ4, or in six phosphorylatable, positionally equivalent amino acid residues of another E2F4 protein as defined by multiple amino acid sequence alignment or in a functionally equivalent variant.

In another embodiment, the methods of the invention comprise determining the phosphorylation of seven threonine residues, namely Thr311, Thr313, Thr76, Thr225, Thr286, Thr391 and Thr40 of dog E2F4 protein with Uniprot database accession number J9NSJ4, or in seven phosphorylatable, positionally equivalent amino acid residues of another E2F4 protein as defined by multiple amino acid sequence alignment or in a functionally equivalent variant.

In another particular embodiment of the methods of the invention, the subject is a dog and phosphorylation is determined for the threonine residue selected from the group consisting of positions 251 (Thr251), 253 (Thr253), 14 (Thr14), 165 (Thr165), 226 (Thr226), 332 (Thr332) and 241 (Thr241), and combinations thereof, of dog E2F4 protein with Uniprot database accession number F1P6Y0, or in a phosphorylatable, positionally equivalent amino acid residue of another E2F4 protein as defined by multiple amino acid sequence alignment or in a functionally equivalent variant.

In a more particular embodiment, the methods of the invention comprise determining the phosphorylation of only one of the threonine residues selected from the group consisting of Thr251, Thr253, Thr14, Thr165, Thr226, Thr332 and Thr241 of dog E2F4 protein with Uniprot database accession number F1P6Y0, or in a phosphorylatable, positionally equivalent amino acid residue of another E2F4 protein as defined by multiple amino acid sequence alignment or in a functionally equivalent variant.

In another embodiment, the methods of the invention comprise determining the phosphorylation of two threonine residues selected from the group consisting of Thr251 and Thr253; Thr251 and Thr14; Thr251 and Thr165; Thr251 and Thr226; Thr251 and Thr332; Thr251 and Thr241; Thr253 and Thr14; Thr253 and Thr165; Thr253 and Thr226; Thr253 and Thr332; Thr253 and Thr241; Thr14 and Thr165; Thr14 and Thr226; Thr14 and Thr332; Thr14 and Thr241; Thr165 and Thr226; Thr165 and Thr332; Thr165 and Thr241; Thr226 and Thr332; Thr226 and Thr241; and Thr332 and Thr241 of dog E2F4 protein with Uniprot database accession number F1P6Y0, or in two phosphorylatable, positionally equivalent amino acid residues of another E2F4 protein as defined by multiple amino acid sequence alignment or in a functionally equivalent variant.

In another embodiment, the methods of the invention comprise determining the phosphorylation of three threonine residues selected from the group consisting of Thr251, Thr253 and Thr14; Thr251, Thr253 and Thr165; Thr251, Thr253 and Thr226; Thr251, Thr253 and Thr332; Thr251, Thr253 and Thr241; Thr251, Thr14 and Thr165; Thr251, Thr14 and Thr226; Thr251, Thr14 and Thr332; Thr251, Thr14 and Thr241; Thr251, Thr165 and Thr226; Thr251, Thr165 and Thr332; Thr251, Thr165 and Thr241; Thr251, Thr226 and Thr332; Thr251, Thr226 and Thr241; Thr251, Thr332 and Thr241; Thr253, Thr14 and Thr165; Thr253, Thr14 and Thr226; Thr253, Thr14 and Thr332; Thr253, Thr14 and Thr241; Thr253, Thr165 and Thr226; Thr253, Thr165 and Thr332; Thr253, Thr165 and Thr241; Thr253, Thr226 and Thr332; Thr253, Thr226 and Thr241; Thr253, Thr332 and Thr241; Thr14, Thr165 and Thr226; Thr14, Thr165 and Thr332; Thr14, Thr165 and Thr241; Thr14, Thr226 and Thr332; Thr14, Thr226 and Thr241; Thr14, Thr332 and Thr241; Thr165, Thr226 and Thr332; Thr165, Thr226 and Thr241; Thr165, Thr332 and Thr241; and Thr226, Thr332 and Thr241 of dog E2F4 protein with Uniprot database accession number F1P6Y0, or in three phosphorylatable, positionally equivalent amino acid residues of another E2F4 protein as defined by multiple amino acid sequence alignment or in a functionally equivalent variant.

In another embodiment, the methods of the invention comprise determining the phosphorylation of four threonine residues selected from the group consisting of Thr251, Thr253, Thr14 and Thr165; Thr251, Thr253, Thr14 and Thr226; Thr251, Thr253, Thr14 and Thr332; Thr251, Thr253, Thr14 and Thr241; Thr251, Thr253, Thr165 and Thr226; Thr251, Thr253, Thr165 and Thr332; Thr251, Thr253, Thr165 and Thr241; Thr251, Thr253, Thr226 and Thr332; Thr251, Thr253, Thr226 and Thr241; Thr251, Thr253, Thr332 and Thr241; Thr251, Thr14, Thr165 and Thr226; Thr251, Thr14, Thr165 and Thr332; Thr251, Thr14, Thr165 and Thr241; Thr251, Thr14, Thr226 and Thr332; Thr251, Thr14, Thr226 and Thr241; Thr251, Thr14, Thr332 and Thr241; Thr251, Thr165, Thr226 and Thr332; Thr251, Thr165, Thr226 and Thr241; Thr251, Thr165, Thr332 and Thr241; Thr251, Thr226, Thr332 and Thr241; Thr253, Thr14, Thr165 and Thr226; Thr253, Thr14, Thr165 and Thr332; Thr253, Thr14, Thr165 and Thr241; Thr253, Thr14, Thr226 and Thr332; Thr253, Thr14, Thr226 and Thr241; Thr253, Thr14, Thr332 and Thr241; Thr253, Thr165, Thr226 and Thr332; Thr253, Thr165, Thr226 and Thr241; Thr253, Thr165, Thr332 and Thr241; Thr253, Thr226, Thr332 and Thr241; Thr14, Thr165, Thr226 and Thr332; Thr14, Thr165, Thr226 and Thr241; Thr14, Thr165, Thr332 and Thr241; Thr14, Thr226, Thr332 and Thr241; and Thr165, Thr226, Thr332 and Thr241 of dog E2F4 protein with Uniprot database accession number F1P6Y0, or in four phosphorylatable, positionally equivalent amino acid residues of another E2F4 protein as defined by multiple amino acid sequence alignment or in a functionally equivalent variant.

In another embodiment, the methods of the invention comprise determining the phosphorylation of five threonine residues selected from the group consisting of Thr251, Thr253, Thr14, Thr165 and Thr226; Thr251, Thr253, Thr14, Thr165 and Thr332; Thr251, Thr253, Thr14, Thr165 and Thr241; Thr251, Thr253, Thr14, Thr226 and Thr332; Thr251, Thr253, Thr14, Thr226 and Thr241; Thr251, Thr253, Thr14, Thr332 and Thr241; Thr251, Thr253, Thr165, Thr226 and Thr332; Thr251, Thr253, Thr165, Thr226 and Thr241; Thr251, Thr253, Thr165, Thr332 and Thr241; Thr251, Thr253, Thr226, Thr332 and Thr241; Thr251, Thr14, Thr165, Thr226 and Thr332; Thr251, Thr14, Thr165, Thr226 and Thr241; Thr251, Thr14, Thr165, Thr332 and Thr241; Thr251, Thr14, Thr226, Thr332 and Thr241; Thr251, Thr165, Thr226, Thr332 and Thr241; Thr253, Thr14, Thr165, Thr226 and Thr332; Thr253, Thr14, Thr165, Thr226 and Thr241; Thr253, Thr14, Thr165, Thr332 and Thr241; Thr253, Thr14, Thr226, Thr332 and Thr241; Thr253, Thr165, Thr226, Thr332 and Thr241; and Thr14, Thr165, Thr226, Thr332 and Thr241 of dog E2F4 protein with Uniprot database accession number F1P6Y0, or in five phosphorylatable, positionally equivalent amino acid residues of another E2F4 protein as defined by multiple amino acid sequence alignment or in a functionally equivalent variant.

In another embodiment, the methods of the invention comprise determining the phosphorylation of six threonine residues selected from the group consisting of Thr251, Thr253, Thr14, Thr165, Thr226 and Thr332; Thr251, Thr253, Thr14, Thr165, Thr226 and Thr241; Thr251, Thr253, Thr14, Thr165, Thr332 and Thr241; Thr251, Thr253, Thr14, Thr226, Thr332 and Thr241; Thr251, Thr253, Thr165, Thr226, Thr332 and Thr241; Thr251, Thr14, Thr165, Thr226, Thr332 and Thr241; and Thr253, Thr14, Thr165, Thr226, Thr332, Thr241 of dog E2F4 protein with Uniprot database accession number F1P6Y0, or in six phosphorylatable, positionally equivalent amino acid residues of another E2F4 protein as defined by multiple amino acid sequence alignment or in a functionally equivalent variant.

In another embodiment, the methods of the invention comprise determining the phosphorylation of seven threonine residues selected from the group consisting of Thr251, Thr253, Thr14, Thr165, Thr226, Thr332 and Thr241 of dog E2F4 protein with Uniprot database accession number F1P6Y0, or in seven phosphorylatable, positionally equivalent amino acid residues of another E2F4 protein as defined by multiple amino acid sequence alignment or in a functionally equivalent variant.

In another embodiment, the methods of the invention comprise determining the mean phosphorylation in threonine residues of dog E2F4 protein using to that end an anti-phosphothreonine antibody. By way of illustration, this determination can be carried out by means of isolating dog E2F4, for example, by means of using anti-dog E2F4 antibodies, followed by quantitative or semi-quantitative immunodetection using antibodies specific against phosphothreonine to that end.

In another embodiment, the methods of the invention comprise determining the phosphorylation in threonine of dog E2F4 protein as detected by means of using anti-phosphothreonine antibodies.

A second step of the methods of the invention comprises comparing the level of phosphorylation obtained in the first step of the methods with a reference value.

As it is used herein, the term "reference value" refers to predetermined criteria used as a reference for evaluating the values or data obtained from the samples collected from a subject. The reference value or reference level can be an absolute value, a relative value, a value having an upper or lower limit, a range of values, an average value, a median value, a mean value, or a value compared to a particular control or baseline value. A reference value can be based on a value of an individual sample such as, for example, a value obtained from a sample from the subject being analyzed, but at an earlier point in time. The reference value can be based on a large number of samples, such as a population of subjects of the matching chronological age group, or based on a pool of samples including or excluding the sample being analyzed. In a particular embodiment, the reference value for a phosphorylated amino acid residue in E2F4 protein is the level of phosphorylation of said residue of the protein in a sample from a subject or population of control subjects, i.e., those that do not exhibit any neurodegenerative disorder, specifically those that do not exhibit Alzheimer's disease or a cognitive disorder similar to said disease. Typical reference samples will generally be obtained from subjects who are clinically well documented.

After the second step of comparison and according to the first method of the invention, an increase in the level of phosphorylation in threonine residues in E2F4 protein or in a functionally equivalent variant compared to a reference value is indicative that said subject has a high risk of developing Alzheimer's or a cognitive disorder similar to said disease.

According to the second method of the invention, an increase in the level of phosphorylation in threonine residues in E2F4 protein or in a functionally equivalent variant compared to the reference value is indicative that said subject is susceptible to receive a therapy for the prevention and/or treatment of Alzheimer's disease or a cognitive disorder similar to said disease.

According to the third method of the invention, an increase in the level of phosphorylation in threonine residues in E2F4 protein or in a functionally equivalent variant compared to the reference value is indicative that said subject is a candidate for receiving a therapy for the prevention and/or treatment of Alzheimer's disease or a cognitive disorder similar to said disease.

As it is used herein, "increase in the level of phosphorylation" refers to the fact that the level of phosphorylation in at least one threonine residue of E2F4 is greater than a reference value. The levels of phosphorylation are considered greater than their reference value when they are greater by at least 1.5%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more compared to the reference value.

Likewise, in the context of the present invention the level of phosphorylation decreases when the level of phosphorylation in a sample is lower than a reference value. The levels of phosphorylation are considered lower than their reference value when they are lower by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150% or more compared to the reference value.

Use as a Risk Marker

In another aspect, the invention relates to the use of E2F4 or a functionally equivalent variant thereof, wherein the E2F4 or variant is phosphorylated in threonine as a marker of the risk of developing Alzheimer's disease or a cognitive disorder similar to Alzheimer's disease.

In a particular embodiment, E2F4 is of human origin and is phosphorylated in the threonine selected from the group consisting of threonine in position 248 (Thr248), threonine in position 250 (Thr250), threonine in position 14 (Thr14), threonine in position 163 (Thr163), threonine in position 224 (Thr224), threonine in position 333 (Thr333) and combinations thereof, and the disease is Alzheimer's disease.

In another more particular embodiment, E2F4 is of human origin and is phosphorylated in one or more threonine residues of human E2F4 protein, namely Thr248, Thr250, Thr14, Thr163, Thr224 and/or Thr333, and the disease is Alzheimer's disease.

In a more particular embodiment, E2F4 is of human origin and is phosphorylated in only one of the threonine residues selected from the group consisting of Thr248, Thr250, Thr14, Thr163, Thr224 and Thr333, and the disease is Alzheimer's disease In another particular embodiment, E2F4 is of human origin and is phosphorylated in two threonine residues selected from the group consisting of Thr248 and Thr250; Thr248 and Thr14; Thr248 and Thr163; Thr248 and Thr224; Thr248 and Thr333; Thr250 and Thr14; Thr250 and Thr163; Thr250 and Thr224; Thr250 and Thr333; Thr14 and Thr163; Thr14 and Thr224; Thr14 and Thr333; Thr163 and Thr224; Thr163 and Thr333; and Thr224 and Thr333, and the disease is Alzheimer's disease.

In another particular embodiment, E2F4 is of human origin and is phosphorylated in three threonine residues selected from the group consisting of Thr248, Thr250 and Thr14; Thr248, Thr250 and Thr163; Thr248, Thr250 and Thr224; Thr248, Thr250 and Thr333; Thr248, Thr14 and Thr163; Thr248, Thr14 and Thr224; Thr248, Thr14 and Thr333; Thr248, Thr163 and Thr224; Thr248, Thr163 and Thr333; Thr248, Thr224 and Thr333; Thr250, Thr14 and Thr163; Thr250, Thr14 and Thr224; Thr250, Thr14 and Thr333; Thr250, Thr163 and Thr224; Thr250, Thr163 and Thr333; Thr250, Thr224 and Thr333; Thr14, Thr163 and Thr224; Thr14, Thr163 and Thr333; Thr14, Thr224 and Thr333; and Thr163, Thr224 and Thr333, and the disease is Alzheimer's disease.

In another particular embodiment, E2F4 is of human origin and is phosphorylated in four threonine residues selected from the group consisting of Thr248, Thr250, Thr14 and Thr163; Thr248, Thr250, Thr14 and Thr224; Thr248, Thr250, Thr14 and Thr333; Thr248, Thr250, Thr163 and Thr224; Thr248, Thr250, Thr163 and Thr333; Thr248, Thr250, Thr224 and Thr333; Thr248, Thr14, Thr163 and Thr224; Thr248, Thr14, Thr163 and Thr333; Thr248, Thr14, Thr224 and Thr333; Thr248, Thr163, Thr224 and Thr333; Thr250, Thr14, Thr163 and Thr224; Thr250, Thr14, Thr163 and Thr333; Thr250, Thr14, Thr224 and Thr333; Thr250, Thr163, Thr224 and Thr333; and Thr14, Thr163, Thr224 and Thr333, and the disease is Alzheimer's disease.

In another particular embodiment, E2F4 is of human origin and is phosphorylated in five threonine residues selected from the group consisting of Thr248, Thr250, Thr14, Thr163 and Thr224; Thr248, Thr250, Thr14, Thr163 and Thr333; Thr248, Thr250, Thr14, Thr224 and Thr333; Thr248, Thr250, Thr163, Thr224 and Thr333; Thr248, Thr14, Thr163, Thr224 and Thr333; and Thr250, Thr14, Thr163, Thr224 and Thr333, and the disease is Alzheimer's disease.

In another particular embodiment, E2F4 is of human origin and is phosphorylated in six threonine residues, namely Thr248, Thr250, Thr14, Thr163, Thr224 and Thr333 of human E2F4 protein, and the disease is Alzheimer's disease.

In another embodiment of the use of E2F4 or a functionally equivalent variant thereof, wherein the E2F4 or variant is phosphorylated in threonine as a marker of the risk of developing Alzheimer's disease or a cognitive disorder similar to Alzheimer's disease, the E2F4 is dog E2F4 with Uniprot database accession number J9NSJ4 and is phosphorylated in the threonine selected from the group consisting of threonine in position 311 (Thr311), threonine in position 313 (Thr313), threonine in position 76 (Thr76), threonine in position 225 (Thr225), threonine in position 286 (Thr286), threonine in position 391 (Thr391), threonine in position 40 (Thr40) and combinations thereof, and the cognitive disorder similar to Alzheimer's disease is cognitive dysfunction syndrome.

In another more particular embodiment, the E2F4 is dog E2F4 with Uniprot database accession number J9NSJ4 and is phosphorylated in one, two, three, four, five or all seven of the threonine residues selected from the group consisting of Thr311, Thr313, Thr76, Thr225, Thr286, Thr391 and Thr40.

The possible combinations of phosphorylated threonine residues of dog E2F4 with Uniprot database accession number J9NSJ4 have been described above in relation to the methods of the invention and are likewise applicable to this aspect.

In another embodiment of the use of E2F4 or a functionally equivalent variant thereof, wherein the E2F4 or variant is phosphorylated in threonine as a marker of the risk of developing Alzheimer's disease or a cognitive disorder similar to Alzheimer's disease, the E2F4 is dog E2F4 with Uniprot database accession number F1P6Y0 and is phosphorylated in the threonine selected from the group consisting of threonine in position 251 (Thr251), threonine in position 253 (Thr253), threonine in position 14 (Thr14), threonine in position 165 (Thr165), threonine in position 226 (Thr226), threonine in position 332 (Thr332) and threonine in position 241 (Thr241), and combinations thereof, and the cognitive disorder similar to Alzheimer's disease is cognitive dysfunction syndrome.

In another more particular embodiment, the E2F4 is dog E2F4 with Uniprot database accession number F1P6Y0 and is phosphorylated in one, two, three, four, five or all seven of the threonine residues selected from the group consisting of Thr251, Thr253, Thr14, Thr165, Thr226, Thr332 and Thr241.

The possible combinations of phosphorylated threonine residues of dog E2F4 with Uniprot database accession number F1P6Y0 have been described above in relation to the methods of the invention and are likewise applicable to this aspect.

The terms described above are likewise applicable to this aspect.

Kit of the Invention

In another aspect, the invention relates to a kit comprising a reagent capable of determining the level of phosphorylation in threonine residues of E2F4 protein for determining the risk of a subject developing Alzheimer's or a cognitive disorder similar to Alzheimer's disease, for designing a personalized therapy in a subject or for selecting a patient susceptible to be treated with a therapy for the prevention and/or treatment of Alzheimer's disease or a cognitive disorder similar to Alzheimer's disease.

As it is used herein, "kit" refers to a product containing the different reagents required for carrying out the methods of the invention packaged so as to allow their transport and storage. Materials suitable for packaging the components of the kit include glass, plastic (polyethylene, polypropylene, polycarbonate and the like), bottles, vials, paper, sachets and the like. Additionally, the kits of the invention can contain instructions for the simultaneous, sequential or separate use of the different components in the kit. Said instructions can be found in the form of a printed material or in the form of an electronic support capable of storing instructions such that they can be read by a subject, such as electronic storage media (magnetic discs, tapes and the like), optical media (CD-ROM, DVD) and the like. Additionally or alternatively, the media can contain Internet addresses which provide said instructions.

As it is used herein, "reagent capable of determining the level of phosphorylation" is understood to be a compound capable of detecting a phosphorylated residue of a protein.

In a particular embodiment, the reagent capable of determining the level of phosphorylation of E2F4 protein is selected from the group consisting of a) a reagent capable of determining the level of phosphorylation in the threonine residue in position 248 (Thr248) of human E2F4 protein or of a functionally equivalent variant in a phosphorylatable, positionally equivalent amino acid residue of another E2F4 protein as defined by multiple amino acid sequence alignment, b) a reagent capable of determining the level of phosphorylation in position 250 (Thr250) of human E2F4 protein or of a functionally equivalent variant in a phosphorylatable, positionally equivalent amino acid residue of another E2F4 protein as defined by multiple amino acid sequence alignment, c) a reagent capable of determining the level of phosphorylation in the threonine residue in position 14 (Thr14) of human E2F4 protein or of a functionally equivalent variant in a phosphorylatable, positionally equivalent amino acid residue of another E2F4 protein as defined by multiple amino acid sequence alignment, d) a reagent capable of determining the level of phosphorylation in the threonine residue in position 163 (Thr163) of human E2F4 protein or of a functionally equivalent variant in a phosphorylatable, positionally equivalent amino acid residue of another E2F4 protein as defined by multiple amino acid sequence alignment, e) a reagent capable of determining the level of phosphorylation in the threonine residue in position 224 (Thr224) of human E2F4 protein or of a functionally equivalent variant in a phosphorylatable, positionally equivalent amino acid residue of another E2F4 protein as defined by multiple amino acid sequence alignment, f) a reagent capable of determining the level of phosphorylation in the threonine residue in position 333 (Thr333) of human E2F4 protein or of a functionally equivalent variant in a phosphorylatable, positionally equivalent amino acid residue of another E2F4 protein as defined by multiple amino acid sequence alignment, g) a reagent capable of determining the level of phosphorylation in Thr of human E2F4 protein or of a functionally equivalent variant in a phosphorylatable, positionally equivalent amino acid residue of another E2F4 protein as defined by multiple amino acid sequence alignment, h) a reagent capable of determining the level of phosphorylation in the threonine residue in position 311 (Thr311) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, i) a reagent capable of determining the level of phosphorylation in the threonine residue in position 313 (Thr313) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, j) a reagent capable of determining the level of phosphorylation in the threonine residue in position 76 (Thr76)

of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, k) a reagent capable of determining the level of phosphorylation in the threonine residue in position 225 (Thr225) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, l) a reagent capable of determining the level of phosphorylation in the threonine residue in position 286 (Thr286) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, m) a reagent capable of determining the level of phosphorylation in the threonine residue in position 391 (Thr391) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, n) a reagent capable of determining the level of phosphorylation in the threonine residue in position 40 (Thr40) of dog E2F4 protein with Uniprot database accession number J9NSJ4 or of a functionally equivalent variant in a phosphorylatable, positionally equivalent amino acid residue of another E2F4 protein as defined by multiple amino acid sequence alignment, o) a reagent capable of determining the level of phosphorylation in Thr in dog E2F4 protein with Uniprot database accession number J9NSJ4, or of a functionally equivalent variant in a phosphorylatable, positionally equivalent amino acid residue of another E2F4 protein as defined by multiple amino acid sequence alignment.

In a particular embodiment, the reagent capable of determining the level of phosphorylation of E2F4 protein is selected from the group consisting of a) a reagent capable of determining the level of phosphorylation in the threonine residue in position 251 (Thr251) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, b) a reagent capable of determining the level of phosphorylation in the threonine residue in position 253 (Thr253) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, c) a reagent capable of determining the level of phosphorylation in the threonine residue in position 14 (Thr14) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, d) a reagent capable of determining the level of phosphorylation in the threonine residue in position 165 (Thr165) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, e) a reagent capable of determining the level of phosphorylation in the threonine residue in position 226 (Thr226) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, f) a reagent capable of determining the level of phosphorylation in the threonine residue in position 332 (Thr332) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, g) a reagent capable of determining the level of phosphorylation in the threonine residue in position 241 (Thr241) of dog E2F4 protein with Uniprot database accession number F1P6Y0 or of a functionally equivalent variant in a phosphorylatable, positionally equivalent amino acid residue of another E2F4 protein as defined by multiple amino acid sequence alignment, h) a reagent capable of determining the level of phosphorylation in Thr in dog E2F4 protein with Uniprot database accession number F1P6Y0, or of a functionally equivalent variant in a phosphorylatable, positionally equivalent amino acid residue of another E2F4 protein as defined by multiple amino acid sequence alignment.

More particularly, the reagent capable of determining the level of phosphorylation in the threonine residue in position 248 (Thr248) of human E2F4 protein is an antibody specifically recognizing a phosphopeptide comprising the human E2F4 sequence which comprises position 248, and wherein said Thr residue is phosphorylated.

In another more particular embodiment, the reagent capable of determining the level of phosphorylation in the threonine residue in position 250 (Thr250) of human E2F4 protein is an antibody specifically recognizing a phosphopeptide comprising the human E2F4 sequence which comprises position 250, and wherein said Thr residue is phosphorylated.

In another particular embodiment, the reagent capable of determining the level of phosphorylation in the threonine residue in position 14 (Thr14) of human E2F4 protein is an antibody specifically recognizing a phosphopeptide comprising the human E2F4 sequence which comprises position 14, and wherein said Thr residue is phosphorylated.

In another more particular embodiment, the reagent capable of determining the level of phosphorylation in the threonine residue in position 163 (Thr163) of human E2F4 protein is an antibody specifically recognizing a phosphopeptide comprising the human E2F4 sequence which comprises position 163, and wherein said Thr residue is phosphorylated.

In another more particular embodiment, the reagent capable of determining the level of phosphorylation in the threonine residue in position 224 (Thr224) of human E2F4 protein is an antibody specifically recognizing a phosphopeptide comprising the human E2F4 sequence which comprises position 224, and wherein said Thr residue is phosphorylated.

In another more particular embodiment, the reagent capable of determining the level of phosphorylation in the threonine residue in position 333 (Thr333) of human E2F4 protein is an antibody specifically recognizing a phosphopeptide comprising the human E2F4 sequence which comprises position 333, and wherein said Thr residue is phosphorylated.

In another more particular embodiment, the reagent capable of determining the level of phosphorylation in Thr of human E2F4 protein is an anti-phosphothreonine antibody.

In another more particular embodiment, the reagent capable of determining the level of phosphorylation in the threonine residue in position 311 (Thr311) of dog E2F4 protein with Uniprot database accession number J9NSJ4 is an antibody specifically recognizing a phosphopeptide comprising the dog E2F4 sequence which comprises position 311, and wherein said Thr residue is phosphorylated.

In another more particular embodiment, the reagent capable of determining the level of phosphorylation in the threonine residue in position 313 (Thr313) of dog E2F4 protein with Uniprot database accession number J9NSJ4 is an antibody specifically recognizing a phosphopeptide comprising the dog E2F4 sequence which comprises position 313, and wherein said Thr residue is phosphorylated.

In another more particular embodiment, the reagent capable of determining the level of phosphorylation in the threonine residue in position 76 (Thr76) of dog E2F4 protein with Uniprot database accession number J9NSJ4 is an antibody specifically recognizing a phosphopeptide comprising the dog E2F4 sequence which comprises position 76, and wherein said Thr residue is phosphorylated.

In another more particular embodiment, the reagent capable of determining the level of phosphorylation in the threonine residue in position 225 (Thr225) of dog E2F4 protein with Uniprot database accession number J9NSJ4 is an antibody specifically recognizing a phosphopeptide comprising the dog E2F4 sequence which comprises position 225, and wherein said Thr residue is phosphorylated.

In another more particular embodiment, the reagent capable of determining the level of phosphorylation in the threonine residue in position 286 (Thr286) of dog E2F4 protein with Uniprot database accession number J9NSJ4 is an antibody specifically recognizing a phosphopeptide comprising the dog E2F4 sequence which comprises position 286, and wherein said Thr residue is phosphorylated.

In another more particular embodiment, the reagent capable of determining the level of phosphorylation in the threonine residue in position 391 (Thr391) of dog E2F4 protein with Uniprot database accession number j9NSJ4 is an antibody specifically recognizing a phosphopeptide comprising the dog E2F4 sequence which comprises position 391, and wherein said Thr residue is phosphorylated.

In another more particular embodiment, the reagent capable of determining the level of phosphorylation in the threonine residue in position 40 (Thr40) of dog E2F4 protein with Uniprot database accession number J9NSJ4 is an antibody specifically recognizing a phosphopeptide comprising the dog E2F4 sequence which comprises position 40, and wherein said Thr residue is phosphorylated.

In another more particular embodiment, the reagent capable of determining the level of phosphorylation in Thr of dog E2F4 protein is an anti-phosphothreonine antibody.

In another more particular embodiment, the reagent capable of determining the level of phosphorylation in the threonine residue in position 251 (Thr251) of dog E2F4 protein with Uniprot database accession number F1P6Y0 is an antibody specifically recognizing a phosphopeptide comprising the dog E2F4 sequence which comprises position 251, and wherein said Thr residue is phosphorylated.

In another more particular embodiment, the reagent capable of determining the level of phosphorylation in the threonine residue in position 253 (Thr253) of dog E2F4 protein with Uniprot database accession number F1P6Y0 is an antibody specifically recognizing a phosphopeptide comprising the dog E2F4 sequence which comprises position 253, and wherein said Thr residue is phosphorylated.

In another more particular embodiment, the reagent capable of determining the level of phosphorylation in the threonine residue in position 14 (Thr14) of dog E2F4 protein with Uniprot database accession number F1P6Y0 is an antibody specifically recognizing a phosphopeptide comprising the dog E2F4 sequence which comprises position 14, and wherein said Thr residue is phosphorylated.

In another more particular embodiment, the reagent capable of determining the level of phosphorylation in the threonine residue in position 165 (Thr165) of dog E2F4 protein with Uniprot database accession number F1P6Y0 is an antibody specifically recognizing a phosphopeptide comprising the dog E2F4 sequence which comprises position 165, and wherein said Thr residue is phosphorylated.

In another more particular embodiment, the reagent capable of determining the level of phosphorylation in the threonine residue in position 226 (Thr226) of dog E2F4 protein with Uniprot database accession number F1P6Y0 is an antibody specifically recognizing a phosphopeptide comprising the dog E2F4 sequence which comprises position 226, and wherein said Thr residue is phosphorylated.

In another more particular embodiment, the reagent capable of determining the level of phosphorylation in the threonine residue in position 332 (Thr332) of dog E2F4 protein with Uniprot database accession number F1P6Y0 is an antibody specifically recognizing a phosphopeptide comprising the dog E2F4 sequence which comprises position 332, and wherein said Thr residue is phosphorylated.

In another more particular embodiment, the reagent capable of determining the level of phosphorylation in the threonine residue in position 241 (Thr241) of dog E2F4 protein with Uniprot database accession number F1P6Y0 is an antibody specifically recognizing a phosphopeptide comprising the dog E2F4 sequence which comprises position 241, and wherein said Thr residue is phosphorylated.

In another embodiment, the kit of the invention comprises one or more reagents mentioned above.

Additionally, the kit of the invention comprises a reagent which is capable of binding specifically to E2F4 protein. In a more particular embodiment, said reagent is an antibody.

As it is used herein, "specific recognition or specific binding," when referring to a peptide or protein with a phosphorylated residue, refers to the fact that said reagent only recognizes the peptide or protein when it is phosphorylated in the residue of interest and does not exhibit any reaction when it is not phosphorylated. When referring to a peptide or protein irrespective of its level of phosphorylation, it refers to the fact that the reagent is capable of reacting with at least one epitope of the peptide or protein, in contrast with a non-specific interaction.

As it is used herein, the term "antibody" can be a natural polyclonal or monoclonal antibody or a non-natural antibody, for example, a single-domain antibody, a single-chain variable-fragment antibody, a microantibody, etc. Methods for producing such antibodies are well known in the art.

In some embodiments, the specific antibodies used in the invention are labeled with a detectable marker (for example, a fluorescent dye or a detectable enzyme), or modified to make detection easier (for example, with biotin to allow for detection with an avidin or streptavidin). In other embodiments, the reagent will not be directly labeled or modified.

In certain embodiments, the kits include the reagents in the form of an array. The array includes at least two different reagents suitable for determining the levels of phosphorylation in one or more residues of interest bound to a substrate in a predetermined pattern (for example, a grid). The present invention therefore provides arrays comprising the reagents suitable for determining the levels of phosphorylation of one or more amino acid residues mentioned in the invention.

The placement of the different reagents (the "capture reagents") allows measuring the levels of phosphorylation of a number of different amino acid residues in the same reaction. Kits including reagents in array form are usually found in sandwich format, so such kits can also contain detection reagents. Different detection reagents are usually included in the kit, where each detection reagent is specific for a different antibody. The detection reagents in such embodiments are usually reagents specific for the same proteins as the reagents bound to the substrate (although the detection reagents typically bind to a different portion or in the protein site of the substrate-bound reagents), and are generally affinity-type detection reagents. Like the detection reagents of any other assay format, the detection reagents can be modified with a detectable residue, modified to allow the separate binding of a detectable residue, or they may not be modified. Array-type kits including detection reagents which are modified or not modified to allow the binding of a detectable residue can also contain additional detectable residues (for example, detectable residues that bind to the detection reagent, such as labeled antibodies binding without modifying detection reagents or streptavidin modified with a detectable residue for biotin detection, modified detection reagents).

The antibodies can be brought about by means of methods known in the art. For example, a mammal such as a mouse, a hamster or a rabbit can be immunized with an immunogenic form of an E2F4 protein phosphorylated in a specific threonine residue (for example, antigenic fragment which can bring about an antibody response, for example a synthetic peptide containing the phosphorylated amino acid). Techniques for conferring immunogenicity to a protein or peptide include vehicle conjugation or other techniques that are very well known in the art. For example, a peptidyl portion of a polypeptide can be administered in the presence of an adjuvant. The progression of immunization can be monitored by detecting plasma or serum antibody titers. Standard ELISA or other immunoassays can be used with the immunogen as an antigen for evaluating the levels of antibodies.

After immunization, antisera that are reactive with a polypeptide can be obtained, and polyclonal antibodies can be isolated from the serum if desired. To produce monoclonal antibodies, antibody-producing cells (lymphocytes) can be collected from an immunized animal and fused using standard methods for fusing somatic cells with immortalizing cells, such as myeloma cells, to give rise to hybridoma cells. Such techniques are very well known in the art and include, for example, the hybridoma technique, such as the human B-cell hybridoma technique and the EVB hybridoma technique for producing human monoclonal antibodies. Hybridoma cells can be immunochemically screened for producing antibodies that are specifically reactive with the polypeptides and isolated monoclonal antibodies.

In another more particular embodiment, the reagent which is capable of binding specifically to E2F4 protein is immobilized on a support.

The terms described above are likewise applicable to this aspect.

Use of the Kits of the Invention

In another aspect, the invention relates to the use of a kit of the invention for determining the risk of a subject developing Alzheimer's disease or a cognitive disorder similar to said disease in a subject, for designing a personalized therapy in a subject suffering from mild cognitive impairment or for selecting a patient susceptible to be treated with a therapy for the prevention and/or treatment of Alzheimer's or a cognitive disorder similar to said disease.

The terms described above are likewise applicable to this aspect.

The invention is now described in detail by means of the following examples provided only to illustrate but not limit the scope of the invention.

Materials and Methods

Mice

Double transgenic mice $APP^{swe}/PS1^{deltaE9}$ (APP/PS1) [Fernandez et al., 2012 Mol. Psychiatry 17, 705-718] and control mice C57BL6/J were used.

Obtaining Blood Serum

The mice were anesthetized with pentobarbital (2 mg/10 g of body weight), and 0.2-0.5 ml of blood were drawn from the right ventricle of said mice by means of a hypodermic needle (25 G) before they were sacrificed by decapitation. The blood samples were stored in heparin-free test tubes and incubated at 37° C. for 1 hour for the purpose of obtaining blood clots. The samples were then incubated at 4° C. for at least 12 hours in order to retract the blood clot. The clot was then removed taking care not to cause any red blood cell lysis, and the samples were centrifuged (4000 rpm) for 15 minutes at 4° C. to remove possible coagulation residues. The supernatants (sera) were put away, frozen at −80° C. for later use.

Tissue Samples

Brain hemicortices of BL6/C57 mice (control) and $APP^{swe}/PS1^{deltaE9}$ mice (APP/PS1) [Fernandez et al., 2012 Mol. Psychiatry. 17: 705-718] sacrificed on postnatal day 0 (P0) or at 2 and 5 months of age (2 m and 5 m, respectively) and kept at −80° C. were used.

Human frontal and parietal cortex samples obtained from Banco de Tejidos Fundación Cien (BT-CIEN, Madrid) and Banco de Cerebros de la Region de Murcia (Hospital Virgen de la Arrixaca, Murcia) and kept at −80° C. were also used. The methods for obtaining the samples have been approved by the Ethics Committee of the Instituto de Salud Carlos III and bioethics subcommittee of the Consejo Superior de Investigaciones Cientificas (Madrid, Spain).

Preparing a Cell Nuclear Suspension 30-40 mg of human cortex or murine brain hemicortex were broken up in a Dounce homogenizer with 3 ml of DNase-free phosphate-buffered saline (PBS) containing 0.1% Triton X-100 (Sigma-Aldrich, T8787) (PBS-T) and cOmplete mini EDTA-free protease inhibitor (Roche Applied Science, 11 836 170 001) according to the manufacturer's indications. The homogenate thus obtained was centrifuged at 4° C. for 2 minutes at 200 g. The volume of the supernatant thus obtained was adjusted to 12 ml with PBS-T and centrifuged at 4° C. for 4 minutes at 400 g. The pellet thus obtained was kept in ice in a total volume of 900 µl of PBS-T for 20 minutes and then gently resuspended by means of pipetting.

Immunofluorescent Labeling of the Nuclear Suspension

The nuclei of the nuclear suspension were immunolabeled with the neuron-specific anti-NeuN antibody (clone A60, Millipore, mab377). A 400 µl aliquot of the nuclear suspension (see above) to which 0.5 mg/mL bovine serum albumin (BSA, Sigma-Aldrich, A4503) and 10% bovine serum (Life Technologies, 16170-086) were incorporated was incubated for 12 hours at 4° C. with the primary anti-NeuN antibody at a dilution of 1:800 and secondary anti-mouse IgG-Alexa 488 at a dilution of 1:500. Another aliquot was incubated under the same conditions without the primary antibody, this aliquot constituting the negative control. After incubation with the antibodies, the sample was filtered (nylon filter with 30 µm pore), the volume thereof was adjusted to 600 µl with PBS containing propidium iodide and RNase for a final concentration of 50 µg/mL and 25 µg/mL, respectively.

Flow Cytometry

The quantification of the percentage of 4 C neurons was carried out by means of flow cytometry using a FACSAria cytometer (BD Biosciences) and its argon excitation laser (488). The emission of the propidium iodide incorporated in the DNA and the signal of fluorophore Alexa-488 associated with anti-NeuN labeling were detected with BP 530/30 and BP 616/23 emission filters, respectively. The selection of the different analyzed populations followed the method described by López-Sánchez and Frade *J. Neurosci.* 33: 7488-7500, 2013.

Statistical Analysis

Cytometry analyses were performed with at least four individuals from each group in at least three replicates for mice and two replicates for humans. The statistical significance was analyzed by means of Student's t-test.

Quantifying E2F4 and E2F4 Phosphorylated in Thr by Means of ELISA

A solution of 20 µg/ml rabbit anti-E2F4 polyclonal antibody (Ref. AP09986PU-N; Acris) in TBS (50 mM Tris-HCl, pH 7.5; 150 mM NaCl) was prepared. Fifty microliters of the preceding solution were added to the bottom of each well of a Microtest™ 96-well plate (Ref 351177; Becton Dickinson). At least six wells were used for each experimental point, three of them for quantifying the relative levels of E2F4 and the remaining three for quantifying the phospho-Thr-E2F4 form. In parallel, 50 µl of TBS were added to the bottom of six other wells for obtaining the background analysis value. Finally, the plate was covered with an adhesive plastic and incubated overnight at 4° C. The solutions were removed from the wells the next day, the wells were washed two times using 200 µl of TBS each time. Then, 150 µl of TBS containing 3% bovine serum albumin (blocking buffer) were added to the bottom of each well, and the plate was covered with an adhesive plastic. The plate was then incubated for at least 2 hours at room temperature. After this incubation, the solutions were removed from the wells, the wells were washed two times using 200 µl of TBS each time. Dilutions of the blood serum in blocking buffer (1/10 dilution) were then prepared, and 50 µl of each dilution were added to the bottom of the wells coated with the rabbit anti-E2F4 polyclonal antibody, as well as to the wells incubated with TBS. The plates were then covered with an adhesive plastic, where they were incubated for at least 4 hours at room temperature. After removing the serum dilutions from the wells, the wells were washed four times using 200 µl of TBS each time. A 1/1000 dilution (in blocking buffer) of the mouse anti-E2F4 monoclonal antibody, clone LLF4-2 (Ref. MABE160; Millipore), was then prepared. This solution was used for evaluating the levels of serum E2F4. Another 1/1000 dilution (in blocking buffer) of mouse anti-phosphoThr monoclonal antibody (clone 20H6.1) (Ref. 05-1923; Millipore) was also prepared. This solution was used for estimating the relative levels of serum phosphoThr-E2F4. After adding 50 µl of these solutions to the bottom of the corresponding wells (for quantifying E2F4 or phospho-Thr-E2F4), the plates were covered with an adhesive plastic and incubated overnight at 4° C. After this period elapsed, the solutions were removed from the wells and the wells were washed four times using 200 µl of TBS. A 1/2000 dilution (in blocking buffer) of goat anti-mouse IgG (H+L)-HRP conjugate (Ref 170-6516; BioRad) was then prepared, and 50 µl of this solution were added to the bottom of each and every one of the analysis wells. The plate was then covered with an adhesive plastic and incubated for at least 2 hours at room temperature. The solutions were then removed from the wells and the wells were washed eight times using 200 µl of TBS. An ABTS tablet (Ref. 11 112 422 001; Roche) was then dissolved in 50 ml of ABTS buffer (Ref. 11 112 597 001; Roche), and 150 µl of this solution were added to the bottom of each and every one of the analysis wells, as well as to three untreated wells for estimating the value of the blank. The plate was then incubated for about 15-45 minutes at room temperature and optical density at 405 nm was quantified in the different wells using an ELISA reader. After subtracting the blank, the values obtained in the wells treated with rabbit anti-E2F4 polyclonal antibody were deducted from those obtained in the wells initially incubated with TBS. The phosphoThr-E2F4 values thus obtained were finally divided by the values obtained for E2F4.

Example 1. Analysis of the Levels of Phosphorylation in Thr Residues of Blood Serum E2F4 of APP/PS1 Mice The brain of Alzheimer's patients undergoes a tetraploidization process similar to that which occurs naturally in neurons during embryonic development and precedes the neuropathological damages defining the pathology (FIG. 1).

Figure 2:
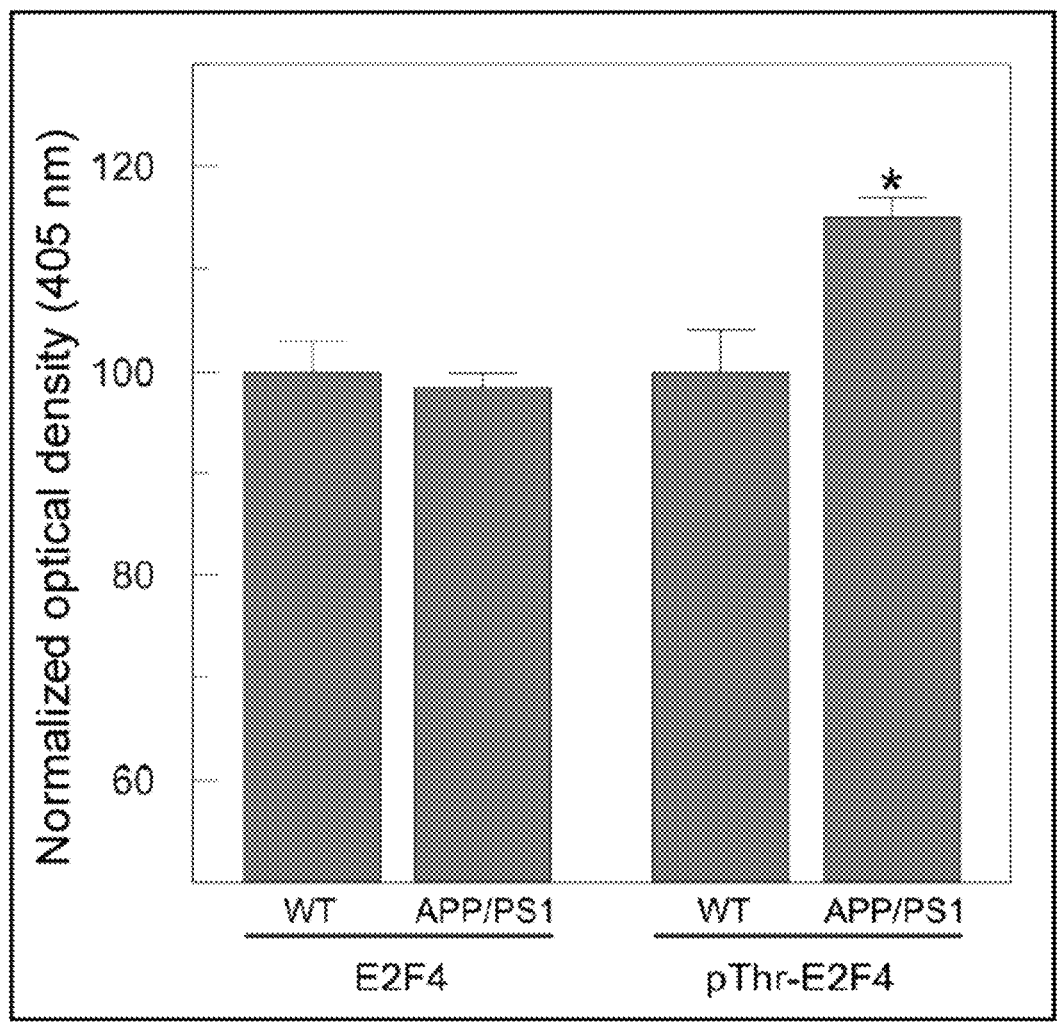
FIG. 2 shows the ELISA quantification, in normalized arbitrary units, of the levels of E2F (E2F4) and E2F4 phosphorylated in Thr residues (pThr-E2F4) present in cerebral cortex extracts of 8-week old wild-type and APP/PS1 mice. *$p<0.05$ (Student's t-test).
Figure 3:
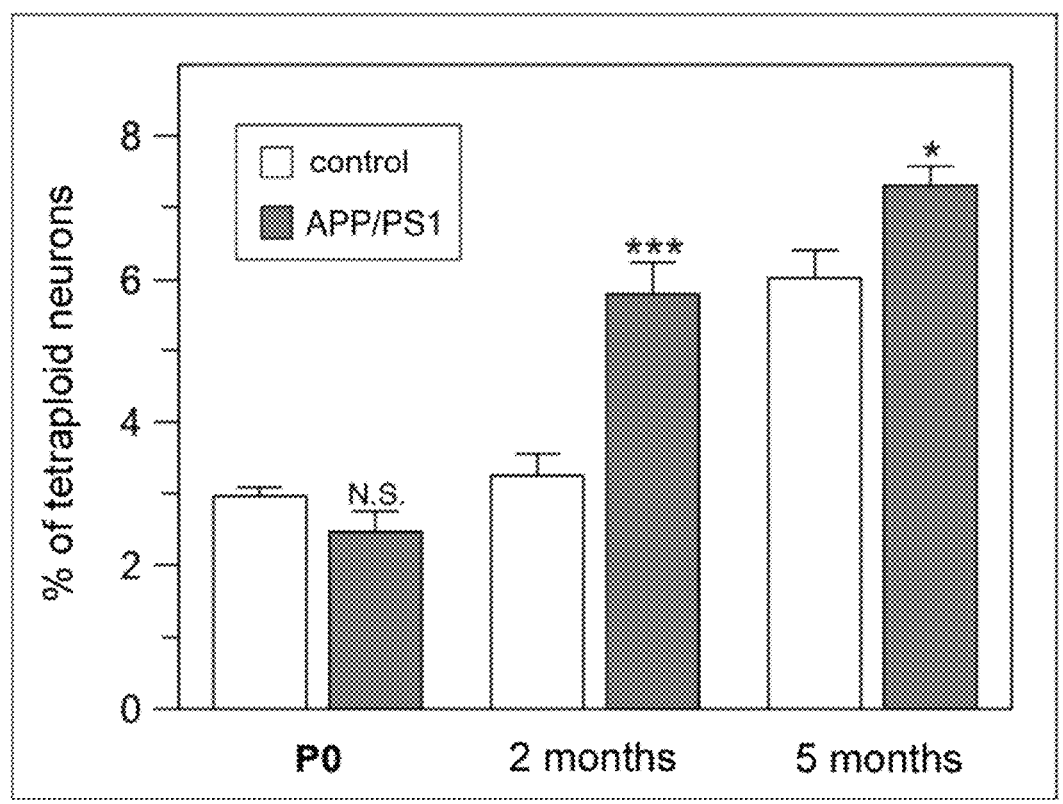
FIG. 3 shows levels of neuronal tetraploidy in frontal and parietal cortex of control mice or APP/PS1 mice (APP/PS1) of the indicated ages, estimated by means of flow cytometry in fresh cell nuclei that are positive for the neuron-specific NeuN antigen. An increase in the percentage of tetraploid neurons in APP/PS1 mice at 2 months of age, prior to the presence of β-amyloid plaques, is observed (Zhang et al., 2012 Neurobiol. Aging 33, 2661-2677).*p<0.05; ***p<0.005 (Student's t-test).

When studying the cerebral cortex of transgenic mice APP/PS1, it is observed that the cerebral cortex of these mice shows a significant increase in the levels of phosphorylation in Thr residues of E2F4 when compared to control mice (FIG. 2). This phenomenon is already observed in eight-week old mice, i.e., long before β-amyloid peptide accumulations and other neuropathological alterations in this murine line, which take place starting from 3.5 months of age, are detected (Zhang et al., 2012 Neurobiol. Aging 33: 2661-2677). Furthermore, this increase in phosphorylation is concomitant with the neuronal tetraploidization process observed in the cerebral cortex of these mice (FIG. 3). Therefore, phosphorylation of E2F4 and neuronal tetraploidization would be the earliest events known, prior to AD.

Figure 4:
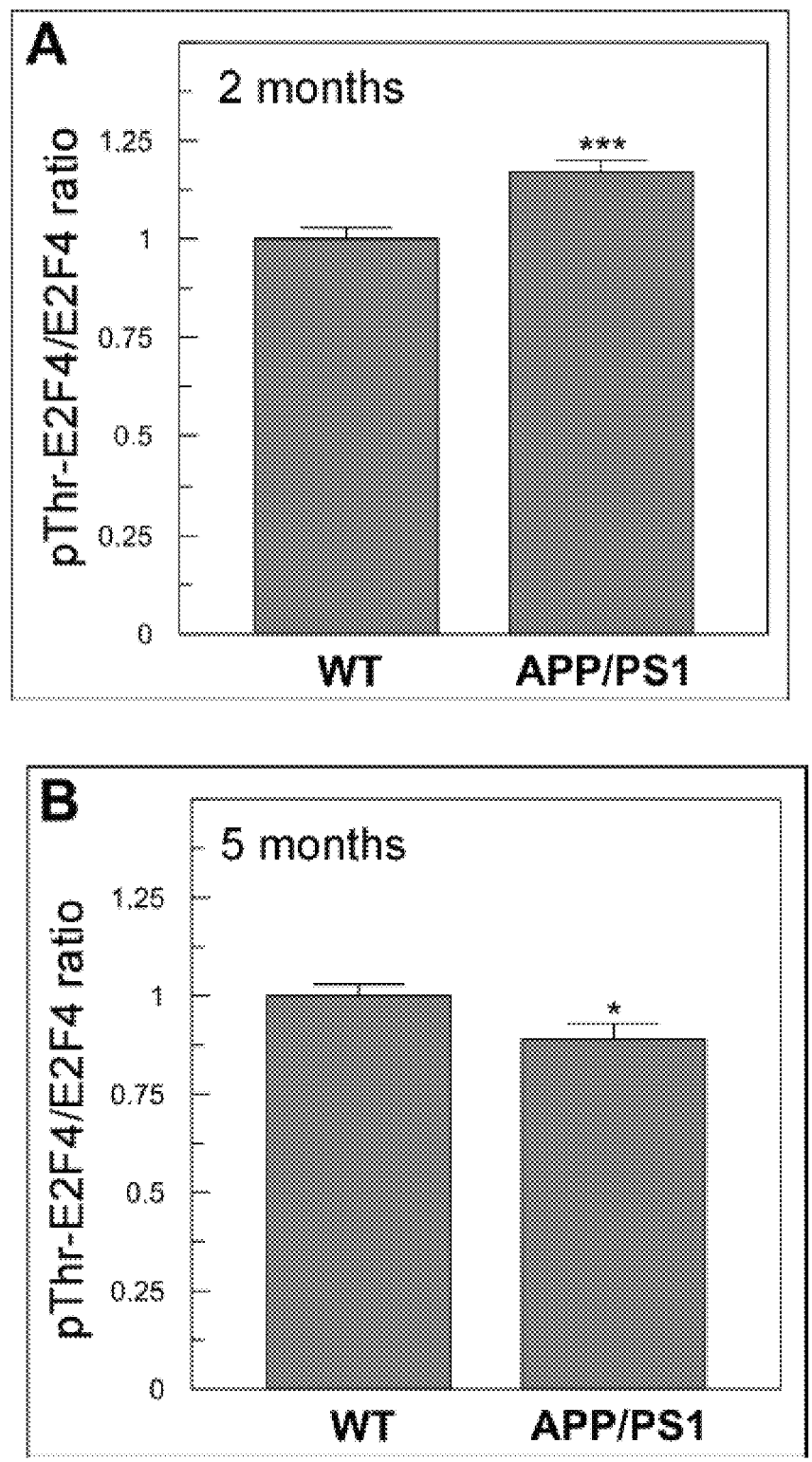
FIG. 4 shows the ELISA quantification of the ratios between E2F4 phosphorylated in Thr residues (pThr-E2F4) and total E2F4 (E2F4) present in the blood serum of 2-month old (A) and 5-month old (B) wild-type and APP/PS1 mice. *p<0.05; ***p<0.005 (Student's t-test).

It can be observed how the levels of phosphoThr-E2F4 increase significantly in the serum of 2-month old APP/PS1 mice (FIG. 4A), right when neuronal tetraploidy is observed to increase substantially (FIG. 3). In contrast, the levels of phosphoThr-E2F4 decrease significantly in the serum of APP/PS1 mice when these mice are 5 months old (FIG. 4B), and the tetraploidization process is greatly reduced (FIG. 3).

Therefore, the increase in the levels of E2F4 phosphorylated in Thr in samples from a patient can be used for the diagnosis of AD (Alzheimer's disease). Furthermore, given that the increase in the levels of E2F4 phosphorylated in Thr occurs at a time point of the disease before the onset of symptoms, this marker can be used for prognostic purposes in order to determine the risk of a subject developing Alzheimer's disease. This can furthermore be carried out in a minimally invasive manner given that the levels of E2F4 phosphorylated in Thr can be detected in plasma and peripheral tissues.

The invention claimed is:

1. A method for determining the risk of developing, in a subject, Alzheimer's disease or cognitive dysfunction syndrome of a dog suffering from mild cognitive impairment and treating said subject with a therapy for the prevention of Alzheimer's disease or a cognitive dysfunction syndrome of a dog which method comprises
   a) obtaining a sample from the subject,
   b) detecting in the sample from the subject whether an increase in the level of phosphorylation in threonine residues in E2F4 protein from human or in E2F4 protein from dog with Uniprot database accession number J9NSJ4 is present in the sample; and
   c) determining the risk of developing Alzheimer's disease or the cognitive dysfunction syndrome of a dog when the presence of an increase in the level of phosphorylation in threonine residues in E2F4 protein in the sample is detected, wherein an increase in the level of phosphorylation in threonine residues in E2F4 protein occurs if the degree of phosphorylation of at least one of the Thr residues in the E2F4 protein is higher than that of a reference value, and wherein the reference value is the level of phosphorylated Thr residue in E2F4 protein in a sample from a subject or population of control subjects; and
   d) treating the subject with a therapy for the prevention of Alzheimer's disease or the cognitive dysfunction syndrome of a dog, wherein the therapy for the prevention of Alzheimer's disease or the cognitive dysfunction syndrome of a dog comprises administering to the subject an effective amount of a therapeutic agent for the prevention of Alzheimer's disease or the cognitive dysfunction syndrome of a dog, wherein the therapeutic agent for the prevention of Alzheimer's disease or the cognitive dysfunction syndrome of a dog is:
      a mutant form of transcription factor E2F4 comprising the amino acid sequence set forth in UniProt Accession No. Q16254, substituted on Thr248 and/or Thr250 residues with an amino acid that cannot be phosphorylated by p38MAPK, or a nucleotide sequence encoding said mutant form.

2. The method according to claim 1, wherein the subject is a human and the therapy is for the prevention of Alzheimer's disease.

3. The method according to claim 1 wherein detecting an increase in the level of phosphorylation in threonine residues in E2F4 protein comprises determining the phosphorylation of the threonine residue selected from the group consisting of threonine residue in position 248 (Thr248), threonine residue in position 250 (Thr250), threonine residue in position 14 (Thr14), threonine residue in position 163 (Thr163), threonine residue in position 224 (Thr224) and threonine residue in position 333 (Thr333), and combinations thereof, of human E2F4 protein,
   or wherein the subject is a dog and wherein the phosphorylation of the threonine residue selected from the group consisting of threonine residue in position 311 (Thr311), threonine residue in position 313 (Thr313), threonine residue in position 76 (Thr76), threonine residue in position 225 (Thr225), threonine residue in position 286 (Thr286), threonine residue in position 391 (Thr391), threonine residue in position 40 (Thr40) and combinations thereof of dog E2F4 protein with Uniprot database accession number J9NSJ4.

4. The method according to claim 1 wherein the sample is selected from the group of cerebrospinal fluid, blood serum, blood plasma, blood and peripheral blood mononuclear cells.

5. The method according to claim 1, wherein the level of phosphorylation is determined by means of ELISA.

6. A method for treating a subject in need of treatment with a therapy for the prevention of Alzheimer's disease or a cognitive dysfunction syndrome of a dog, the method comprising administering an effective amount of the therapy for the prevention of Alzheimer's disease or the cognitive dysfunction syndrome of a dog, wherein a sample from the subject has previously been tested to detect an increase in the level of phosphorylation in threonine residues in E2F4 protein from human or in dog E2F4 protein from with Uniprot database accession number J9NSJ4, wherein an increase in the level of phosphorylation in threonine residues in E2F4 protein occurs if the degree of phosphorylation of at least one of the Thr residues in the E2F4 protein is higher than that of a reference value, wherein the reference value is the level of phosphorylated Thr residue in E2F4 protein in a sample from a subject or population of control subjects and wherein the therapeutic agent for the prevention of Alzheimer's disease or the cognitive dysfunction syndrome of a dog is selected from the group consisting of:
   a mutant form of transcription factor E2F4 comprising the amino acid sequence set forth in UniProt Accession No. Q16254, substituted on Thr248 and/or Thr250 residues with an amino acid that cannot be phosphorylated by p38MAPK, or a nucleotide sequence encoding said mutant form.

7. The method according to claim 6 wherein determining the level of phosphorylation in threonine residues in E2F4 protein comprises determining the phosphorylation of the threonine residue selected from the group consisting of threonine residue in position 248 (Thr248), threonine residue in position 250 (Thr250), threonine residue in position 14 (Thr14), threonine residue in position 163 (Thr163), threonine residue in position 224 (Thr224) and threonine residue in position 333 (Thr333), and combinations thereof, of human E2F4 protein, ; or
   wherein the subject is a dog and wherein the phosphorylation of the threonine residue selected from the group consisting of threonine residue in position 311 (Thr311), threonine residue in position 313 (Thr313), threonine residue in position 76 (Thr76), threonine residue in position 225 (Thr225), threonine residue in position 286 (Thr286), threonine residue in position 391 (Thr391), threonine residue in position 40 (Thr40) and combinations thereof of dog E2F4 protein with Uniprot database accession number J9NSJ4.

8. The method according to claim 6 wherein the sample is selected from the group of cerebrospinal fluid, blood serum, blood plasma, blood and peripheral blood mononuclear cells.

9. The method according to claim 6, wherein the level of phosphorylation is determined by means of ELISA.

* * * * *